United States Patent
de Canniere

(10) Patent No.: US 10,307,167 B2
(45) Date of Patent: **\*Jun. 4, 2019**

(54) ASSEMBLY AND METHOD FOR LEFT ATRIAL APPENDAGE OCCLUSION

(71) Applicant: CorQuest Medical, Inc., Mont-Saint-Guibert (BE)

(72) Inventor: Didier de Canniere, Miami Beach, FL (US)

(73) Assignee: CorQuest Medical, Inc., Mont-Saint-Guibert (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/838,199

(22) Filed: Mar. 15, 2013

(65) Prior Publication Data

US 2014/0172005 A1    Jun. 19, 2014

Related U.S. Application Data

(63) Continuation-in-part of application No. 13/714,989, filed on Dec. 14, 2012.

(51) Int. Cl.
*A61B 17/12*    (2006.01)
*A61B 17/00*    (2006.01)

(52) U.S. Cl.
CPC .... *A61B 17/12122* (2013.01); *A61B 17/1214* (2013.01); *A61B 17/12168* (2013.01);
(Continued)

(58) Field of Classification Search
CPC   A61B 2017/00632; A61B 2017/00575; A61B 2017/00597; A61B 2017/00601;
(Continued)

(56) References Cited

U.S. PATENT DOCUMENTS 3,587,567 A    6/1971   Schiff
4,536,893 A    8/1985   Parravicini
(Continued)

FOREIGN PATENT DOCUMENTS

EP    0577400 B1    10/1999
EP    1147743       10/2001
(Continued)

OTHER PUBLICATIONS http://www.mikebladder.org/oldwine/chm1045/notes/Periodic/Metals/Period06.htm,1996,accessed May 14, 2015.
(Continued)

*Primary Examiner* — Darwin P Erezo
*Assistant Examiner* — Erich Herbermann
(74) *Attorney, Agent, or Firm* — Wolf, Greenfield & Sacks, P.C.

(57) ABSTRACT

An assembly and method for performing the occlusion of the left atrial appendage including a delivery instrument being positioned in communicating relation with the interior of the left atrial appendage and disposing a distal end portion of the delivery instrument in covering relation to the entrance thereof. Occlusion material is movably connected to the delivery instrument and includes at least one elongated single strand of flexible material. A length of the single strand is progressively fed through the delivery instrument into the interior of the left atrial appendage and the flexibility thereof is sufficient to progressively form an arbitrarily intermingled array of occlusion material therein. The dimension and configuration of the formed arbitrarily intermingled array is sufficient to fill a predetermined portion of the interior of the left atrial appendage and thereby conform to the configuration thereof.

19 Claims, 15 Drawing Sheets

(52) U.S. Cl.
CPC .......... *A61B 17/12177* (2013.01); *A61B 2017/00575* (2013.01); *A61B 2017/00592* (2013.01); *A61B 2017/00597* (2013.01); *A61B 2017/00623* (2013.01); *A61B 2017/00632* (2013.01); *A61B 2017/12054* (2013.01)

(58) Field of Classification Search
CPC .. A61B 2017/00606; A61B 2017/0061; A61B 2017/00623; A61B 2017/00592; A61B 17/12122; A61B 17/12168; A61B 17/12177; A61B 17/1214
USPC ........................................ 606/157, 158, 200
See application file for complete search history.

(56) References Cited

U.S. PATENT DOCUMENTS

| | | | |
|---|---|---|---|
| 4,690,134 | A | 9/1987 | Snyders |
| 4,809,694 | A | 3/1989 | Ferrara |
| 5,201,742 | A | 4/1993 | Hasson |
| 5,591,170 | A | 1/1997 | Spievack et al. |
| 5,702,421 | A | 12/1997 | Schneidt |
| 5,924,424 | A | 7/1999 | Stevens et al. |
| 6,063,070 | A | 5/2000 | Eder |
| 6,123,084 | A | 9/2000 | Jandak et al. |
| 6,206,907 | B1 | 3/2001 | Marino et al. |
| 6,328,757 | B1 | 12/2001 | Matheny |
| 6,383,174 | B1* | 5/2002 | Eder ................. 606/1 |
| 6,425,911 | B1 | 7/2002 | Akerfeldt et al. |
| 6,508,828 | B1 | 1/2003 | Akerfeldt et al. |
| 6,537,290 | B2 | 3/2003 | Adams et al. |
| 6,596,012 | B2 | 7/2003 | Akerfeldt et al. |
| 6,616,596 | B1 | 9/2003 | Milbocker |
| 6,641,592 | B1 | 11/2003 | Sauer |
| 6,682,489 | B2 | 1/2004 | Tenerz et al. |
| 6,712,837 | B2 | 3/2004 | Åkerfeldt et al. |
| 6,802,851 | B2* | 10/2004 | Jones et al. ........... 606/200 |
| 6,811,560 | B2 | 11/2004 | Jones et al. |
| 6,902,522 | B1 | 6/2005 | Walsh |
| 6,929,655 | B2 | 8/2005 | Egnelöv et al. |
| 6,958,044 | B2 | 10/2005 | Burbank et al. |
| 6,960,220 | B2 | 11/2005 | Marino et al. |
| 7,044,916 | B2 | 5/2006 | Tenerz et al. |
| 7,445,626 | B2 | 11/2008 | Songer |
| 7,854,743 | B2 | 12/2010 | Palasis et al. |
| 8,092,363 | B2 | 1/2012 | Leinsing |
| 8,133,168 | B2 | 3/2012 | Monnet |
| 8,147,542 | B2 | 4/2012 | Maisano et al. |
| 8,408,214 | B2 | 4/2013 | Spenser |
| 8,506,624 | B2 | 8/2013 | Vidlund |
| 8,758,393 | B2 | 6/2014 | Zentgraf |
| 8,790,394 | B2 | 7/2014 | Miller |
| 9,566,443 | B2 | 2/2017 | de Cannier |
| 2002/0058925 | A1 | 5/2002 | Kaplan et al. |
| 2002/0100485 | A1 | 8/2002 | Stevens et al. |
| 2002/0161378 | A1 | 10/2002 | Downing |
| 2002/0183787 | A1 | 12/2002 | Wahr |
| 2003/0120337 | A1 | 6/2003 | Van Tassel et al. |
| 2004/0087831 | A1 | 5/2004 | Michels et al. |
| 2004/0102804 | A1 | 5/2004 | Chin |
| 2004/0106945 | A1 | 6/2004 | Thramann et al. |
| 2004/0116897 | A1 | 6/2004 | Aboul-Hosn |
| 2004/0138526 | A1 | 7/2004 | Guenst |
| 2004/0138527 | A1 | 7/2004 | Bonner et al. |
| 2004/0143277 | A1 | 7/2004 | Marino et al. |
| 2005/0137700 | A1 | 6/2005 | Spence |
| 2005/0149108 | A1 | 7/2005 | Cox |
| 2006/0074484 | A1 | 4/2006 | Huber |
| 2006/0135962 | A1 | 6/2006 | Kick et al. |
| 2006/0241655 | A1 | 10/2006 | Viola |
| 2006/0247672 | A1 | 11/2006 | Vidlund et al. |
| 2007/0055206 | A1 | 3/2007 | To |
| 2007/0135826 | A1 | 6/2007 | Zaver et al. |
| 2007/0162066 | A1 | 7/2007 | Lyon |
| 2007/0239108 | A1 | 10/2007 | Albrecht et al. |
| 2007/0265643 | A1 | 11/2007 | Beane et al. |
| 2008/0033241 | A1 | 2/2008 | Peh et al. |
| 2008/0114342 | A1 | 5/2008 | Whayne et al. |
| 2008/0140116 | A1 | 6/2008 | Bonutti |
| 2008/0249420 | A1 | 10/2008 | Crossman |
| 2008/0275295 | A1 | 11/2008 | Gertner |
| 2008/0281350 | A1* | 11/2008 | Sepetka ............ A61B 17/0057 606/200 |
| 2009/0005800 | A1 | 1/2009 | Franer |
| 2009/0105751 | A1 | 4/2009 | Zentgraf |
| 2009/0182188 | A1 | 7/2009 | Marseille et al. |
| 2009/0192598 | A1 | 7/2009 | Lattouf |
| 2010/0042147 | A1 | 2/2010 | Janovsky |
| 2010/0161042 | A1 | 6/2010 | Maisano et al. |
| 2010/0161043 | A1 | 6/2010 | Maisano |
| 2010/0179574 | A1 | 7/2010 | Longoria et al. |
| 2010/0228077 | A1 | 9/2010 | Lenker et al. |
| 2010/0274091 | A1 | 10/2010 | Rothstein et al. |
| 2010/0324586 | A1* | 12/2010 | Miles et al. .................. 606/198 |
| 2011/0029071 | A1 | 2/2011 | Zlotnick et al. |
| 2011/0060182 | A1 | 3/2011 | Kassab et al. |
| 2011/0137234 | A1 | 6/2011 | Farnan et al. |
| 2011/0166413 | A1 | 7/2011 | Alferness |
| 2011/0184439 | A1 | 7/2011 | Anderson et al. |
| 2011/0190811 | A1 | 8/2011 | Shanley |
| 2012/0029556 | A1 | 2/2012 | Masters |
| 2012/0143209 | A1 | 6/2012 | Brecheen et al. |
| 2012/0238968 | A1 | 9/2012 | Toy et al. |
| 2012/0245416 | A1 | 9/2012 | Viola |
| 2012/0272452 | A1 | 11/2012 | Schultz |
| 2012/0272495 | A1 | 11/2012 | Hildebrandt et al. |
| 2012/0272497 | A1 | 11/2012 | Smith |
| 2012/0272499 | A1 | 11/2012 | Schley et al. |
| 2012/0272523 | A1 | 11/2012 | Calla et al. |
| 2012/0272555 | A1 | 11/2012 | Heath |
| 2012/0272556 | A1 | 11/2012 | Brown |
| 2012/0272595 | A1 | 11/2012 | Gallant |
| 2012/0272603 | A1 | 11/2012 | Carbines |
| 2012/0272611 | A1 | 11/2012 | Tsukimoto et al. |
| 2012/0272624 | A1 | 11/2012 | Argeriou et al. |
| 2012/0272632 | A1 | 11/2012 | Lans |
| 2012/0272637 | A1 | 11/2012 | Holland et al. |
| 2012/0272652 | A1 | 11/2012 | Nicholls et al. |
| 2012/0272653 | A1 | 11/2012 | Merrill et al. |
| 2012/0272660 | A1 | 11/2012 | Garrett |
| 2012/0272661 | A1 | 11/2012 | Milburn |
| 2012/0272662 | A1 | 11/2012 | Milburn |
| 2012/0272667 | A1 | 11/2012 | Ferraro et al. |
| 2012/0272670 | A1 | 11/2012 | Choi et al. |
| 2012/0272705 | A1 | 11/2012 | Hirane |
| 2012/0272738 | A1 | 11/2012 | Klessel et al. |
| 2012/0272741 | A1 | 11/2012 | Xiao et al. |
| 2012/0272768 | A1 | 11/2012 | Schmidt et al. |
| 2012/0272780 | A1 | 11/2012 | Schimings et al. |
| 2012/0272815 | A1 | 11/2012 | Lingel et al. |
| 2012/0272817 | A1 | 11/2012 | Lindh, Sr. et al. |
| 2012/0272841 | A1 | 11/2012 | Heymanns et al. |
| 2012/0272843 | A1 | 11/2012 | Graff |
| 2012/0272845 | A1 | 11/2012 | Loiret-Bernal et al. |
| 2012/0272846 | A1 | 11/2012 | Fleischer et al. |
| 2012/0272876 | A1 | 11/2012 | Bergeron et al. |
| 2012/0272893 | A1 | 11/2012 | Lauerhaas et al. |
| 2012/0272968 | A1 | 11/2012 | Kirschner |
| 2012/0272996 | A1 | 11/2012 | Jimenez et al. |
| 2012/0273014 | A1 | 11/2012 | Tadayon |
| 2012/0273064 | A1 | 11/2012 | Ismert et al. |
| 2012/0273078 | A1 | 11/2012 | Hawwa et al. |
| 2012/0273079 | A1 | 11/2012 | Guclucan |
| 2012/0273141 | A1 | 11/2012 | Miller et al. |
| 2012/0273142 | A1 | 11/2012 | Miller et al. |
| 2012/0273143 | A1 | 11/2012 | Fillmore et al. |
| 2012/0273161 | A1 | 11/2012 | Raver |
| 2012/0273174 | A1 | 11/2012 | Barnes |
| 2012/0273178 | A1 | 11/2012 | Wanni et al. |
| 2012/0273209 | A1 | 11/2012 | Austin et al. |
| 2012/0273210 | A1 | 11/2012 | Arizmendi, Jr. et al. |
| 2012/0273214 | A1 | 11/2012 | Donald et al. |
| 2012/0273219 | A1 | 11/2012 | Hoffman et al. |
| 2012/0273220 | A1 | 11/2012 | Ezekiel et al. |

(56) References Cited

U.S. PATENT DOCUMENTS

| | | |
|---|---|---|
| 2012/0273228 A1 | 11/2012 | Allouche |
| 2012/0273230 A1 | 11/2012 | Patterson et al. |
| 2012/0273231 A1 | 11/2012 | Whiddon |
| 2012/0273232 A1 | 11/2012 | O'Blenes |
| 2012/0273328 A1 | 11/2012 | Sejourne |
| 2012/0273358 A1 | 11/2012 | Lamoy et al. |
| 2012/0273389 A1 | 11/2012 | Aziz et al. |
| 2012/0273399 A1 | 11/2012 | Daboub et al. |
| 2012/0273438 A1 | 11/2012 | Nordin et al. |
| 2012/0273439 A1 | 11/2012 | Beavers et al. |
| 2012/0273458 A1 | 11/2012 | Bret et al. |
| 2012/0273467 A1 | 11/2012 | Baxter et al. |
| 2012/0273470 A1 | 11/2012 | Zediker et al. |
| 2012/0273518 A1 | 11/2012 | Greer, Jr. |
| 2012/0273555 A1 | 11/2012 | Flak et al. |
| 2012/0273580 A1 | 11/2012 | Warren et al. |
| 2012/0273641 A1 | 11/2012 | Gorman et al. |
| 2012/0273647 A1 | 11/2012 | Moruzzi |
| 2012/0273680 A1 | 11/2012 | Furry |
| 2012/0273843 A1 | 11/2012 | Kim |
| 2012/0273860 A1 | 11/2012 | Chen et al. |
| 2012/0273880 A1 | 11/2012 | Teng et al. |
| 2012/0273902 A1 | 11/2012 | Lin et al. |
| 2012/0273955 A1 | 11/2012 | Or-Bach et al. |
| 2012/0273987 A1 | 11/2012 | Belcher et al. |
| 2012/0273989 A1 | 11/2012 | Graf |
| 2012/0273993 A1 | 11/2012 | Shoseyov et al. |
| 2012/0274001 A1 | 11/2012 | Prabhu |
| 2012/0274020 A1 | 11/2012 | Daboub |
| 2012/0274061 A1 | 11/2012 | Wilkinson |
| 2012/0274065 A1 | 11/2012 | Knapp |
| 2012/0274068 A1 | 11/2012 | Hanback |
| 2012/0274076 A1 | 11/2012 | Kelaiditis et al. |
| 2012/0274145 A1 | 11/2012 | Taddeo |
| 2012/0274198 A1 | 11/2012 | Jenek |
| 2012/0274202 A1 | 11/2012 | Komatsu |
| 2012/0274212 A1 | 11/2012 | Yu et al. |
| 2012/0274256 A1 | 11/2012 | O'Rourke |
| 2012/0274266 A1 | 11/2012 | Yip |
| 2012/0274279 A1 | 11/2012 | Banos et al. |
| 2012/0274280 A1 | 11/2012 | Yip et al. |
| 2012/0274281 A1 | 11/2012 | Kim |
| 2012/0274288 A1 | 11/2012 | Wegener |
| 2012/0274332 A1 | 11/2012 | Sinha et al. |
| 2012/0274391 A1 | 11/2012 | Kim |
| 2012/0274395 A1 | 11/2012 | Deam |
| 2012/0274440 A1 | 11/2012 | Meadows et al. |
| 2012/0274470 A1 | 11/2012 | Sandvick |
| 2012/0274477 A1 | 11/2012 | Prammer |
| 2012/0274769 A1 | 11/2012 | Lee |
| 2012/0274770 A1 | 11/2012 | Lee |
| 2012/0274772 A1 | 11/2012 | Fosburgh et al. |
| 2012/0274870 A1 | 11/2012 | Liu |
| 2012/0274937 A1 | 11/2012 | Hays et al. |
| 2012/0274962 A1 | 11/2012 | Thomas et al. |
| 2012/0275056 A1 | 11/2012 | McGuire, Jr. |
| 2012/0275057 A1 | 11/2012 | McGuire, Jr. |
| 2012/0275085 A1 | 11/2012 | Wilson et al. |
| 2012/0275128 A1 | 11/2012 | Takada et al. |
| 2012/0275140 A1 | 11/2012 | Feinbloom et al. |
| 2012/0275236 A1 | 11/2012 | Hess et al. |
| 2012/0275244 A1 | 11/2012 | Do |
| 2012/0275247 A1 | 11/2012 | Hwang et al. |
| 2012/0275248 A1 | 11/2012 | Won |
| 2012/0275249 A1 | 11/2012 | Yang et al. |
| 2012/0275298 A1 | 11/2012 | Bryant et al. |
| 2012/0275299 A1 | 11/2012 | Taylor et al. |
| 2012/0275338 A1 | 11/2012 | Filsfils et al. |
| 2012/0275356 A1 | 11/2012 | Aharony et al. |
| 2012/0275670 A1 | 11/2012 | Joglekar |
| 2012/0275754 A1 | 11/2012 | Krampotich et al. |
| 2012/0275841 A1 | 11/2012 | Jimenez et al. |
| 2012/0275843 A1 | 11/2012 | Jimenez et al. |
| 2012/0275845 A1 | 11/2012 | Etling |
| 2012/0275860 A1 | 11/2012 | Exline |
| 2012/0275861 A1 | 11/2012 | Myslowski et al. |
| 2012/0275862 A1 | 11/2012 | Vitale |
| 2012/0275881 A1 | 11/2012 | Mueller |
| 2012/0275913 A1 | 11/2012 | Robertson, Jr. et al. |
| 2012/0275924 A1 | 11/2012 | Perkinson |
| 2012/0275927 A1 | 11/2012 | Rhim |
| 2012/0275970 A1 | 11/2012 | Nash et al. |
| 2012/0275999 A1 | 11/2012 | Bell et al. |
| 2012/0276005 A1 | 11/2012 | Yang et al. |
| 2012/0276008 A1 | 11/2012 | Walkenhorst et al. |
| 2012/0276009 A1 | 11/2012 | Pfeifer et al. |
| 2012/0276011 A1 | 11/2012 | Kupussamy et al. |
| 2012/0276021 A1 | 11/2012 | Kumar et al. |
| 2012/0276025 A1 | 11/2012 | Florence et al. |
| 2012/0276041 A1 | 11/2012 | Salamone et al. |
| 2012/0276053 A1 | 11/2012 | Kim |
| 2012/0276061 A1 | 11/2012 | Grazia et al. |
| 2012/0276062 A1 | 11/2012 | Kellar et al. |
| 2012/0276064 A1 | 11/2012 | Blau et al. |
| 2012/0276067 A1 | 11/2012 | Westenfelder |
| 2012/0276068 A1 | 11/2012 | Sabaawy |
| 2012/0276069 A1 | 11/2012 | Karperien et al. |
| 2012/0276071 A1 | 11/2012 | Fraser, Jr. |
| 2012/0276073 A1 | 11/2012 | Schachner et al. |
| 2012/0276074 A1 | 11/2012 | Scharenberg et al. |
| 2012/0276080 A1 | 11/2012 | Kinoshita et al. |
| 2012/0276084 A1 | 11/2012 | Schaumberg et al. |
| 2012/0276087 A1 | 11/2012 | Schafer et al. |
| 2012/0276088 A1 | 11/2012 | El-Deiry et al. |
| 2012/0276089 A1 | 11/2012 | Lee et al. |
| 2012/0276101 A1 | 11/2012 | Kwak et al. |
| 2012/0276103 A1 | 11/2012 | Karperien et al. |
| 2012/0276104 A1 | 11/2012 | Woisetschlager |
| 2012/0276110 A1 | 11/2012 | Simard |
| 2012/0276111 A1 | 11/2012 | Hafezi-Moghadam |
| 2012/0276126 A1 | 11/2012 | Varadhachary et al. |
| 2012/0276130 A1 | 11/2012 | Ros et al. |
| 2012/0276139 A1 | 11/2012 | Moormann et al. |
| 2012/0276143 A1 | 11/2012 | O'Mahony et al. |
| 2012/0276144 A1 | 11/2012 | Kernodle et al. |
| 2012/0276149 A1 | 11/2012 | Littman et al. |
| 2012/0276150 A1 | 11/2012 | Lauritzen et al. |
| 2012/0276151 A1 | 11/2012 | Lewis et al. |
| 2012/0276152 A1 | 11/2012 | Hossainy et al. |
| 2012/0276161 A1 | 11/2012 | Gravagna et al. |
| 2012/0276164 A1 | 11/2012 | Tuominen et al. |
| 2012/0276169 A1 | 11/2012 | Kang et al. |
| 2012/0276173 A1 | 11/2012 | Marcum et al. |
| 2012/0276182 A1 | 11/2012 | Baker, Jr. et al. |
| 2012/0276185 A1 | 11/2012 | Hossainy et al. |
| 2012/0276188 A1 | 11/2012 | Barrows |
| 2012/0276189 A1 | 11/2012 | Johnson |
| 2012/0276193 A1 | 11/2012 | Graversen et al. |
| 2012/0276201 A1 | 11/2012 | Trachtman |
| 2012/0276202 A1 | 11/2012 | Selim et al. |
| 2012/0276203 A1 | 11/2012 | Selim et al. |
| 2012/0276204 A1 | 11/2012 | Remington et al. |
| 2012/0276213 A1 | 11/2012 | Chen |
| 2012/0276218 A1 | 11/2012 | Jung et al. |
| 2012/0276232 A1 | 11/2012 | Marczyk et al. |
| 2012/0276237 A1 | 11/2012 | Heymanns et al. |
| 2012/0276278 A1 | 11/2012 | Qiu et al. |
| 2012/0276286 A1 | 11/2012 | Vijayakumar |
| 2012/0276296 A1 | 11/2012 | Fieberg et al. |
| 2012/0276297 A1 | 11/2012 | Cypcar et al. |
| 2012/0276304 A1 | 11/2012 | Derrien |
| 2012/0276330 A1 | 11/2012 | Durney et al. |
| 2012/0276365 A1 | 11/2012 | Petuskey et al. |
| 2012/0276375 A1 | 11/2012 | Colgan et al. |
| 2012/0276381 A1 | 11/2012 | Cypcar |
| 2012/0276427 A1 | 11/2012 | Kim |
| 2012/0276463 A1 | 11/2012 | Grannell et al. |
| 2012/0276465 A1 | 11/2012 | Paganelli |
| 2012/0276469 A1 | 11/2012 | Shizuku |
| 2012/0276509 A1 | 11/2012 | Iannotti et al. |
| 2012/0276518 A1 | 11/2012 | Gillis |
| 2012/0276522 A1 | 11/2012 | Huang et al. |
| 2012/0276528 A1 | 11/2012 | Cargill et al. |
| 2012/0276529 A1 | 11/2012 | Galisson et al. |

(56) References Cited

U.S. PATENT DOCUMENTS

| | | |
|---|---|---|
| 2012/0276537 A1 | 11/2012 | Kühn et al. |
| 2012/0276552 A1 | 11/2012 | Lu |
| 2012/0276553 A1 | 11/2012 | Gronthos et al. |
| 2012/0276554 A1 | 11/2012 | Gutteridge et al. |
| 2012/0276555 A1 | 11/2012 | Kuhn et al. |
| 2012/0276558 A1 | 11/2012 | Soper et al. |
| 2012/0276572 A1 | 11/2012 | Shekdar et al. |
| 2012/0276581 A1 | 11/2012 | Arav et al. |
| 2012/0276588 A1 | 11/2012 | Hallen-Adams et al. |
| 2012/0276591 A1 | 11/2012 | Kneissel et al. |
| 2012/0276618 A1 | 11/2012 | Dayton et al. |
| 2012/0276626 A1 | 11/2012 | Shogbon et al. |
| 2012/0276627 A1 | 11/2012 | Kelnar et al. |
| 2012/0276628 A1 | 11/2012 | Khan et al. |
| 2012/0276632 A1 | 11/2012 | Strunk et al. |
| 2012/0276679 A1 | 11/2012 | Wu |
| 2012/0276694 A1 | 11/2012 | Koezuka et al. |
| 2012/0276754 A1 | 11/2012 | Cordingley et al. |
| 2012/0276887 A1 | 11/2012 | Romine et al. |
| 2012/0276928 A1 | 11/2012 | Shutter |
| 2012/0277006 A1 | 11/2012 | Kim |
| 2012/0277008 A1 | 11/2012 | Kitchen et al. |
| 2012/0277051 A1 | 11/2012 | Cooper et al. |
| 2012/0277073 A1 | 11/2012 | Bartsch |
| 2012/0277093 A1 | 11/2012 | Andrew et al. |
| 2012/0277110 A1 | 11/2012 | Andre et al. |
| 2012/0277111 A1 | 11/2012 | Crabtree et al. |
| 2012/0277112 A1 | 11/2012 | Linn et al. |
| 2012/0277118 A1 | 11/2012 | Bhati et al. |
| 2012/0277120 A1 | 11/2012 | Serber et al. |
| 2012/0277144 A1 | 11/2012 | Duckers |
| 2012/0277152 A1 | 11/2012 | Ringeisen et al. |
| 2012/0277155 A1 | 11/2012 | VanAntwerp et al. |
| 2012/0277156 A1 | 11/2012 | Gross et al. |
| 2012/0277157 A1 | 11/2012 | Hillman |
| 2012/0277161 A1 | 11/2012 | Agrez et al. |
| 2012/0277162 A1 | 11/2012 | Krasnoperov et al. |
| 2012/0277173 A1 | 11/2012 | Eidenberger |
| 2012/0277179 A1 | 11/2012 | Bhargava |
| 2012/0277195 A1 | 11/2012 | Banov et al. |
| 2012/0277203 A1 | 11/2012 | Lasley et al. |
| 2012/0277204 A1 | 11/2012 | Taniguchi et al. |
| 2012/0277205 A1 | 11/2012 | Badorc et al. |
| 2012/0277210 A1 | 11/2012 | Catron et al. |
| 2012/0277215 A1 | 11/2012 | Ksander et al. |
| 2012/0277228 A1 | 11/2012 | Sutton et al. |
| 2012/0277229 A1 | 11/2012 | Bearss et al. |
| 2012/0277251 A1 | 11/2012 | Palladino et al. |
| 2012/0277265 A1 | 11/2012 | Deraeve et al. |
| 2012/0277269 A1 | 11/2012 | Reilly |
| 2012/0277271 A1 | 11/2012 | Nadeson et al. |
| 2012/0277277 A1 | 11/2012 | Wallace et al. |
| 2012/0277279 A1 | 11/2012 | Barnett et al. |
| 2012/0277282 A1 | 11/2012 | Gotthardt et al. |
| 2012/0277288 A1 | 11/2012 | Drumm et al. |
| 2012/0277307 A1 | 11/2012 | Waddell |
| 2012/0277309 A1 | 11/2012 | Severa et al. |
| 2012/0277312 A1 | 11/2012 | Mink et al. |
| 2012/0277316 A1 | 11/2012 | Tillman et al. |
| 2012/0277319 A1 | 11/2012 | Steigerwald et al. |
| 2012/0277324 A1 | 11/2012 | Burk et al. |
| 2012/0277364 A1 | 11/2012 | Lolli et al. |
| 2012/0277376 A1 | 11/2012 | Baker, Jr. et al. |
| 2012/0277382 A1 | 11/2012 | Booth et al. |
| 2012/0277412 A1 | 11/2012 | Furusako et al. |
| 2012/0277430 A1 | 11/2012 | Taniguchi et al. |
| 2012/0277431 A1 | 11/2012 | Taniguchi et al. |
| 2012/0277451 A1 | 11/2012 | Ochiai |
| 2012/0277453 A1 | 11/2012 | Franklin et al. |
| 2012/0277517 A1 | 11/2012 | Ivkov et al. |
| 2012/0277521 A1 | 11/2012 | Chamberlin |
| 2012/0277522 A1 | 11/2012 | Shalon et al. |
| 2012/0277523 A1 | 11/2012 | Shalon et al. |
| 2012/0277537 A1 | 11/2012 | Kucklick et al. |
| 2012/0277544 A1 | 11/2012 | Femandes et al. |
| 2012/0277546 A1 | 11/2012 | Soykan et al. |
| 2012/0277567 A1 | 11/2012 | Harlev et al. |
| 2012/0277572 A1 | 11/2012 | Hubbard |
| 2012/0277574 A1 | 11/2012 | Panescu |
| 2012/0277576 A1 | 11/2012 | Lui |
| 2012/0277578 A1 | 11/2012 | Gunday et al. |
| 2012/0277582 A1 | 11/2012 | Mafi |
| 2012/0277584 A1 | 11/2012 | Tanaka et al. |
| 2012/0277592 A1 | 11/2012 | Zelenka et al. |
| 2012/0277599 A1 | 11/2012 | Greenhut |
| 2012/0277600 A1 | 11/2012 | Greenhut |
| 2012/0277618 A1 | 11/2012 | Giftakis et al. |
| 2012/0277621 A1 | 11/2012 | Gerber et al. |
| 2012/0277624 A1 | 11/2012 | Cucin |
| 2012/0277626 A1 | 11/2012 | Burbank et al. |
| 2012/0277638 A1 | 11/2012 | Skelton et al. |
| 2012/0277639 A1 | 11/2012 | Pollock et al. |
| 2012/0277642 A1 | 11/2012 | Smith et al. |
| 2012/0277668 A1 | 11/2012 | Chawla |
| 2012/0277671 A1 | 11/2012 | Fuentes |
| 2012/0277672 A1 | 11/2012 | Pepper et al. |
| 2012/0277674 A1 | 11/2012 | Clark, III et al. |
| 2012/0277693 A1 | 11/2012 | Bailey |
| 2012/0277716 A1 | 11/2012 | Ali et al. |
| 2012/0277718 A1 | 11/2012 | Campbell et al. |
| 2012/0277720 A1 | 11/2012 | Humes et al. |
| 2012/0277725 A1 | 11/2012 | Kassab et al. |
| 2012/0277729 A1 | 11/2012 | Melsheimer |
| 2012/0277730 A1 | 11/2012 | Salahieh et al. |
| 2012/0277736 A1 | 11/2012 | Francischelli |
| 2012/0277740 A1 | 11/2012 | Wamking et al. |
| 2012/0277741 A1 | 11/2012 | Davalos et al. |
| 2012/0277743 A1 | 11/2012 | Vallittu |
| 2012/0277746 A1 | 11/2012 | Morgan et al. |
| 2012/0277749 A1 | 11/2012 | Mootien et al. |
| 2012/0277752 A1 | 11/2012 | Wasielewski |
| 2012/0277753 A1 | 11/2012 | Linderman et al. |
| 2012/0277756 A1 | 11/2012 | Ray et al. |
| 2012/0277766 A1 | 11/2012 | Ferree |
| 2012/0277770 A1 | 11/2012 | Fenton et al. |
| 2012/0277771 A1 | 11/2012 | Vaz et al. |
| 2012/0277772 A1 | 11/2012 | Aben et al. |
| 2012/0277773 A1 | 11/2012 | Sargeant et al. |
| 2012/0277774 A1 | 11/2012 | Guo |
| 2012/0277776 A1 | 11/2012 | Kraemer et al. |
| 2012/0277781 A1 | 11/2012 | Gertner |
| 2012/0277784 A1 | 11/2012 | Berez et al. |
| 2012/0277785 A1 | 11/2012 | Aggerholm et al. |
| 2012/0277786 A1 | 11/2012 | Mohl |
| 2012/0277791 A1 | 11/2012 | Abo-Auda et al. |
| 2012/0277792 A1 | 11/2012 | Teeslink et al. |
| 2012/0277793 A1 | 11/2012 | Marczyk et al. |
| 2012/0277798 A1 | 11/2012 | Benson et al. |
| 2012/0277800 A1 | 11/2012 | Jackson |
| 2012/0277807 A1 | 11/2012 | Myung et al. |
| 2012/0277811 A1 | 11/2012 | Lauchner et al. |
| 2012/0277812 A1 | 11/2012 | Kraus |
| 2012/0277814 A1 | 11/2012 | Schuler |
| 2012/0277820 A1 | 11/2012 | Wu et al. |
| 2012/0277823 A1 | 11/2012 | Gerber et al. |
| 2012/0277825 A1 | 11/2012 | Mawson et al. |
| 2012/0277833 A1 | 11/2012 | Gerber et al. |
| 2012/0277835 A1 | 11/2012 | Della Santina et al. |
| 2012/0277837 A1 | 11/2012 | Schuler |
| 2012/0277843 A1 | 11/2012 | Weber et al. |
| 2012/0277845 A1 | 11/2012 | Bowe |
| 2012/0277846 A1 | 11/2012 | Schreck et al. |
| 2012/0277852 A1 | 11/2012 | Shukla et al. |
| 2012/0277853 A1 | 11/2012 | Rothstein |
| 2012/0277854 A1 | 11/2012 | Ryan |
| 2012/0277855 A1 | 11/2012 | Lashinski et al. |
| 2012/0277856 A1 | 11/2012 | Spenser et al. |
| 2012/0277862 A1 | 11/2012 | Tornier et al. |
| 2012/0277864 A1 | 11/2012 | Brodke et al. |
| 2012/0277865 A1 | 11/2012 | Trieu et al. |
| 2012/0277867 A1 | 11/2012 | Kana et al. |
| 2012/0277872 A1 | 11/2012 | Kana et al. |
| 2012/0277873 A1 | 11/2012 | Kana et al. |
| 2012/0277879 A1 | 11/2012 | Ripamonti |

(56) References Cited

U.S. PATENT DOCUMENTS

| | | |
|---|---|---|
| 2012/0277880 A1 | 11/2012 | Winslow et al. |
| 2012/0277882 A1 | 11/2012 | Huang et al. |
| 2012/0277896 A1 | 11/2012 | Uekita et al. |
| 2012/0277903 A1 | 11/2012 | Schaefer |
| 2012/0277939 A1 | 11/2012 | Kumar |
| 2012/0277940 A1 | 11/2012 | Kumar et al. |
| 2012/0277949 A1 | 11/2012 | Ghimire et al. |
| 2012/0277979 A1 | 11/2012 | Kato et al. |
| 2012/0277998 A1 | 11/2012 | Bevilacqua et al. |
| 2012/0277999 A1 | 11/2012 | Somogyi et al. |
| 2012/0278032 A1 | 11/2012 | Chen |
| 2012/0278098 A1 | 11/2012 | Vovan et al. |
| 2012/0278099 A1 | 11/2012 | Kelly et al. |
| 2012/0278123 A1 | 11/2012 | Houle |
| 2012/0278144 A1 | 11/2012 | Popilock et al. |
| 2012/0278195 A1 | 11/2012 | Joseph |
| 2012/0278200 A1 | 11/2012 | van Coppenolle et al. |
| 2012/0278236 A1 | 11/2012 | Jain et al. |
| 2012/0278242 A1 | 11/2012 | Griffith |
| 2012/0278411 A1 | 11/2012 | Lavine |
| 2012/0278439 A1 | 11/2012 | Ahiska et al. |
| 2012/0278454 A1 | 11/2012 | Stewart et al. |
| 2012/0278484 A1 | 11/2012 | Westphal |
| 2012/0278520 A1 | 11/2012 | Barrenscheen et al. |
| 2012/0278554 A1 | 11/2012 | Eilert |
| 2012/0278592 A1 | 11/2012 | Tran |
| 2012/0278597 A1 | 11/2012 | De Atley et al. |
| 2012/0278654 A1 | 11/2012 | Shen et al. |
| 2012/0278657 A1 | 11/2012 | Baker et al. |
| 2012/0278676 A1 | 11/2012 | Teraura |
| 2012/0278684 A1 | 11/2012 | Eldredge et al. |
| 2012/0278689 A1 | 11/2012 | Tamo et al. |
| 2012/0278760 A1 | 11/2012 | Cerny et al. |
| 2012/0278771 A1 | 11/2012 | Ren |
| 2012/0278799 A1 | 11/2012 | Starks et al. |
| 2012/0278865 A1 | 11/2012 | Sawdy |
| 2012/0278913 A1 | 11/2012 | Fraser |
| 2012/0278947 A1 | 11/2012 | Guo et al. |
| 2012/0278957 A1 | 11/2012 | Phan et al. |
| 2012/0283520 A1 | 11/2012 | Kleyman |
| 2012/0283758 A1 | 11/2012 | Miller |
| 2013/0041395 A1 | 2/2013 | De Canniere |
| 2013/0066275 A1 | 3/2013 | De Canniere |
| 2013/0090684 A1 | 4/2013 | Van Bladel et al. |
| 2014/0088417 A1 | 3/2014 | Alhumaid |
| 2014/0100604 A1 | 4/2014 | Litvack et al. |
| 2014/0142687 A1 | 5/2014 | Canniere et al. |
| 2014/0142689 A1 | 5/2014 | de Canniere et al. |
| 2014/0172004 A1 | 6/2014 | Canniere |
| 2015/0025312 A1 | 1/2015 | Canniere |
| 2015/0039023 A1 | 2/2015 | Canniere et al. |
| 2015/0148590 A1 | 5/2015 | Canniere |

FOREIGN PATENT DOCUMENTS

| | | |
|---|---|---|
| EP | 1169968 | 1/2002 |
| EP | 1222896 | 7/2002 |
| EP | 1266626 | 12/2002 |
| EP | 1269919 | 1/2003 |
| EP | 1254634 | 7/2003 |
| EP | 1244725 | 7/2005 |
| EP | 1773239 B1 | 3/2010 |
| EP | 2 363 075 A1 | 9/2011 |
| JP | 2012-200597 A | 10/2012 |
| JP | 2013-523408 A | 6/2013 |
| JP | 2013-536036 A | 9/2013 |
| WO | WO 96/32882 A1 | 10/1996 |
| WO | WO 02/069783 A2 | 9/2002 |
| WO | WO 2009/045265 A1 | 4/2009 |
| WO | WO 2009/137755 A2 | 11/2009 |
| WO | WO 2011/130456 A1 | 10/2011 |
| WO | WO 2011/163666 A1 | 12/2011 |
| WO | WO 2012/025927 A2 | 3/2012 |
| WO | WO 2012 040865 | 4/2012 |
| WO | WO2012040865 A1 | 4/2012 |
| WO | WO 2012/106398 A1 | 8/2012 |
| WO | WO2012016398 A1 | 9/2012 |
| WO | WO 2013/023016 | 2/2013 |
| WO | WO 2013036742 | 3/2013 |
| WO | WO2015081053 A1 | 6/2015 |

OTHER PUBLICATIONS

Mike Blaber, Metals, Non-Metals, and Metalloids, http://www.mikeblaber.org/oldwine/chm 1045/notes/Periodic/Metals/Period06.htm, 1996, accessed May 14, 2015.

International Search Report and Written Opinion dated Oct. 26, 2012 in connection with International Application No. PCT/US2012/050066.

International Preliminary Report on Patentability dated Feb. 20, 2014 in connection with International Application No. PCT/US2012/050066.

International Search Report and Written Opinion dated Mar. 28, 2014 in connection with International Application No. PCT/US2013/070254.

International Preliminary Report on Patentability dated Jun. 25, 2015 in connection with International Application No. PCT/US2013/070254.

International Search Report and Written Opinion dated Jan. 28, 2015 in connection with International Application No. PCT/US2014/062856.

International Preliminary Report on Patentability dated May 12, 2016 in connection with International Application No. PCT/US2014/062856.

International Search Report and Written Opinion dated May 5, 2015 for corresponding International Application No. PCT/US2015/012426.

International Preliminary Report on Patentability dated Aug. 18, 2016 for corresponding International Application No. PCT/US2015/012426.

Extended European Search Report dated Jun. 30, 2016 in connection with European Application No. 13862921.7.

Extended European Search Report dated Jun. 23, 2017 in connection with European Application No. 14857755.4.

Extended European Search Report dated Aug. 17, 2017 in connection with European Application No. 15746528.7.

Australian Examination Report dated Jul. 23, 2018 in connection with Australian Application No. 2014342390.

Canadian Office Communication dated Mar. 8, 2018 in connection with Canadian Application No. 2,938,000.

English translation of Japanese Office Action dated Jul. 25, 2017 in connection with Japanese Application No. 2016-550499.

Mexican Office Action dated Jan. 22, 2016 in connection with Mexican Application No. MX/a/2014/001480.

* cited by examiner

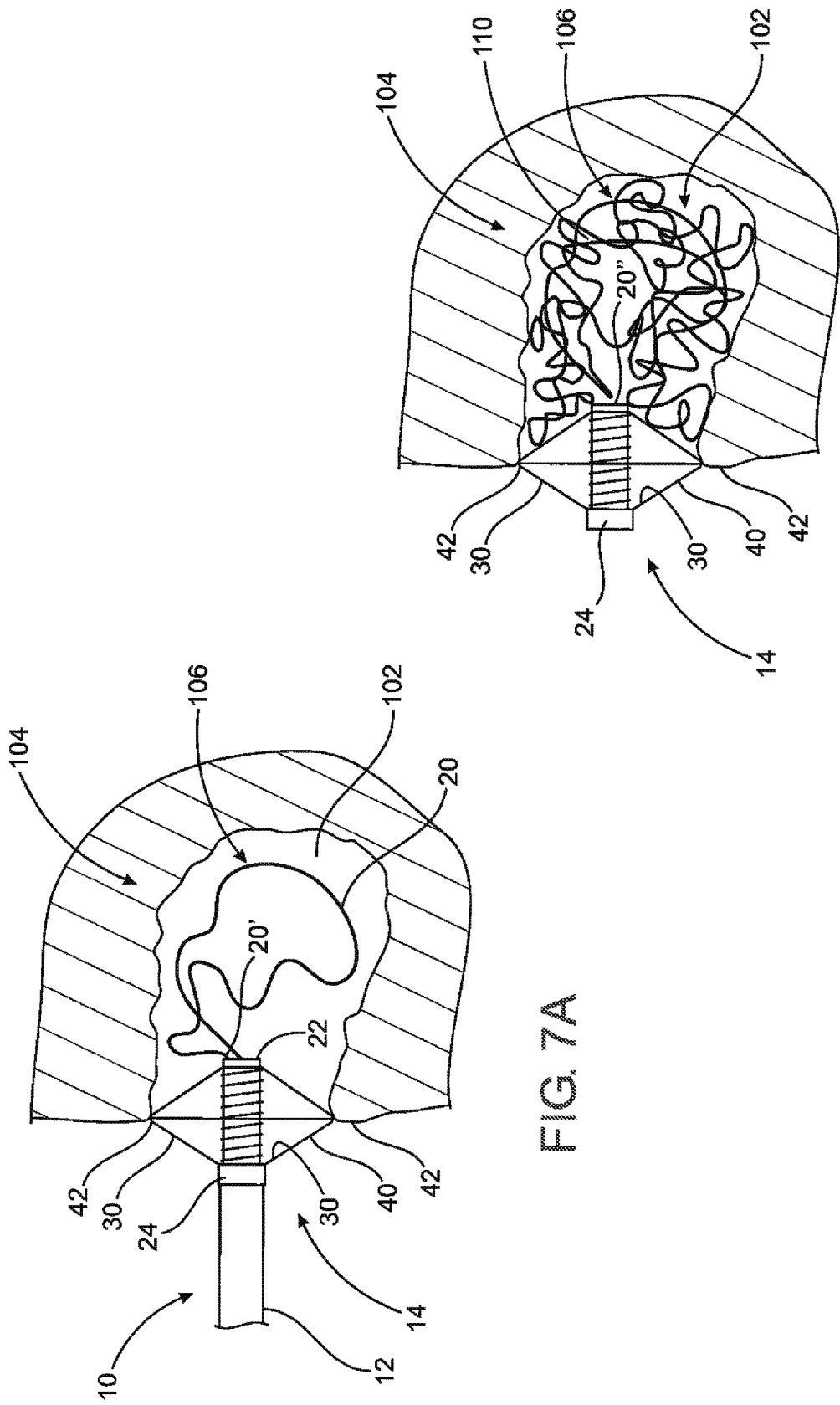

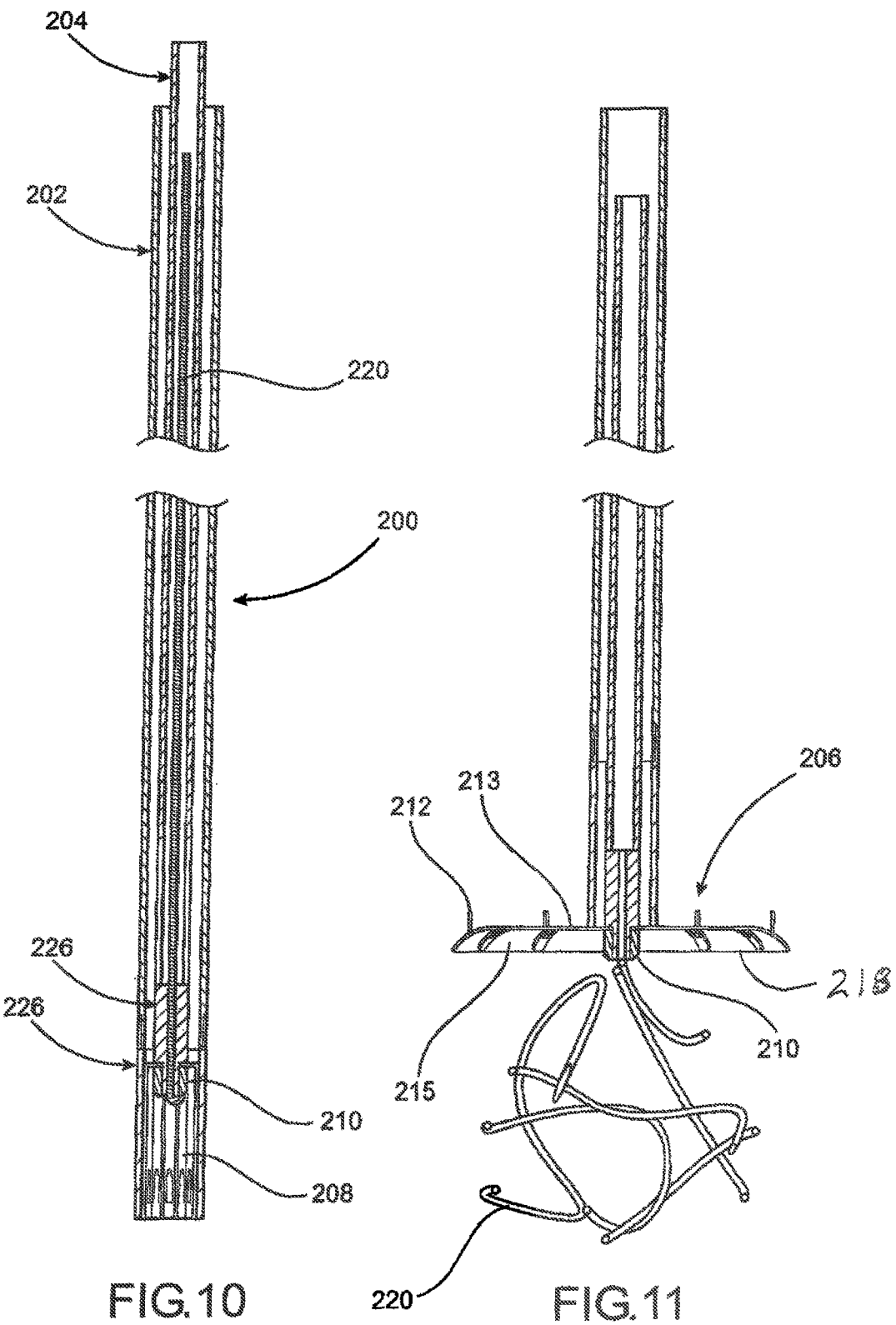

ASSEMBLY AND METHOD FOR LEFT ATRIAL APPENDAGE OCCLUSION

CLAIM OF PRIORITY

The present application is a continuation-in-part application of previously filed, now pending application having Ser. No. 13/714,989, filed on Dec. 14, 2012.

BACKGROUND OF THE INVENTION

Field of the Invention

This invention is directed to an assembly and method for performing the occlusion of a left atrial appendage of the heart and includes a delivery instrument having occlusion material movably connected thereto and disposable outwardly therefrom. The occlusion material comprises at least one elongated single strand of flexible material having sufficient flexibility to progressively form an arbitrarily intermingled array of occlusion material within the interior of the left atrial appendage as it is progressively fed therein in a manner which substantially fills and conforms to the interior configuration thereof.

Description of the Related Art

The left atrial appendage (LAA) is a muscular pouch connected to the left atrium of the heart. It functions as a reservoir for the left atrium but may present serious consequences or problems to the individual when blood pools therein. Such pooling of blood in the appendage may arise spontaneously or due to atrial fibrillation and may result in the formation of blood clots. Moreover, the exiting of the formed blood clot from the interior of the left atrial appendage into the blood stream can cause serious problems when they embolize in the arterial system. Importantly, embolization of these clots is a frequent cause of stroke. Accordingly, it is extremely important to prevent such blood clot formation and/or the migration of a formed clot from the interior of the left atrial appendage in order to reduce the possibility of stroke occurrence, especially in patients with atrial fibrillation.

One common method of reducing the risk of clot formation is the treatment of an individual with anticoagulants such as but not limited to Warfarin. While this method has been generally effective in reducing the occurrence of strokes in a treated patient, such strokes may still occur if there is a necessary or inadvertent lapse of treatment. An additional disadvantage or problem in the anticoagulant treatment is the fact that it is contraindicated in some patients. Another method of treatment in trying to reduce clotting and embolization leading to a stroke includes left atrial appendage obliteration. Obliteration procedures may occur during open cardiac surgery or, less invasively, during thoracoscopic procedure. However, it is recognized that numerous patients with a high risk of stroke are not candidates for such procedures because of a compromised status in their health.

Due to the disadvantages and problems with the above noted treatment procedures, extensive developmental advancements have been attempted with left atrial appendage occlusion. This is a treatment strategy which is directed to the prevention of blood clot formation within the interior of the left atrial appendage. Known occlusion procedures include the use of the "WATCHMAN device" manufactured by Atritech, Inc., of Plymouth Minn., which is intended for use in patients with non-valvular atrial fibrillation (AF) where heart surgery is a backup. Another device commonly termed "PLAATO" (Percutaneous Left Atrial Appendage Transcatether Occlusion) was generally recognized as the first left atrial appendage occlusion device. Both of the above noted LAA occlusion systems are introduced into the right atrium and are then passed into the left atrium through a patent formen ovale or through a puncture hole in the septum wall.

Known and/or recognized adverse events and limitations of the above noted procedures include pericardial effusion, incomplete LAA closure, dislodgment of the occluding device, blood clot formation on the device itself, requiring prolonged oral anticoagulation administration, as well as the general risks associated with catheter based techniques, such as air embolism.

Accordingly, there is a need in the medical arts for an effective procedure for overcoming the dangers associated with blood clot migration within the interior of the left atrial appendage. Such a proposed and improved treatment procedure should be reliable, safe and overcome the disadvantages and problems associated with known treatments of the type set forth above.

SUMMARY OF THE INVENTION

The present invention is directed to an assembly and method for performing an occlusion of the left atrial appendage in a safe and effective manner which overcomes many of the disadvantages associated with known medical techniques for preventing blood clot migration from the interior of the left atrial appendage.

Accordingly, one or more preferred embodiments of the present invention comprise a delivery instrument including a distal end portion. The delivery instrument is structured to dispose the distal end portion in aligned and/or communicating relation with the left atrial appendage including the entrance thereof. In addition, occlusion material comprising at least one elongated, single strand of flexible material is movably mounted on or connected to the delivery instrument and positioned therewith through the heart into communicating relation with the interior of the left atrial appendage.

In at least one preferred embodiment of the present invention the occlusion material comprises a single strand of elongated, flexible material such as, but not limited to, nitinol wire. Its cooperative disposition and structuring relative to the delivery instrument and distal end portion facilitates a portion of the length of the one single strand of occlusion material to be movable along a portion of the delivery instrument and preferably through an interior lumen thereof. Similarly, the length of the single strand is movable outwardly from and preferably through the distal end portion into the interior of the left atrial appendage. In more specific terms, at least a portion of the length of the one single strand of occlusion material is movably disposed on or within the delivery instrument and is progressively movable through the distal end as it is fed into the interior of the left atrial appendage. Upon entry and due at least in part to the flexibility as well as the progressive feeding or passage thereof, the one single strand of occlusion material will form an "arbitrarily intermingled array" of the occlusion material within the interior of the left atrial appendage, as an additional amount or length of the single strand enters the appendage interior.

It is emphasized that the terminology used herein, specifically including "arbitrarily intermingled array", when referring to the occlusion material within the appendage interior, may be accurately described as various portions of the length of the single strand being folded, looped, curled, etc., about itself as the interior of the appendage progressively begins to fill. Accordingly, the location and/or position of the various portions of the length within the appendage interior, relative to each other and to the interior surfaces or portions of the appendage, will always be inconsistently disposed and therefore "arbitrarily intermingled" or intermixed with one another, such as when applied to different left atrial appendages of different patients. Further, the various portions of the length of the single strand, forming the arbitrary intermingled array, are not connected or attached to one another or to the interior tissue portions of the left atrial appendage.

Therefore, the single strand of occlusion material will differ from conventional occlusion devices known in the art. More specifically, the single strand of occlusion material will not be formed into a consistently structured frame, network, pattern or like occluding device, having a substantially predetermined configuration, shape or size, as the single strand is progressively fed into the interior of the left atrial appendage. In contrast, the at least one single strand of occlusion material, due at least in part to its flexibility as well as its progressive entry into the appendage interior, will form differently shaped and dimensioned "arrays" of occlusion material comprising intermixed, folded, overlapping, curled, etc. segments of the length of the single strand each time it is applied to the left atrial appendage of a different patient. As should be apparent, the "arbitrarily intermixed array" of occlusion material may also be of different dimensions and configurations dependent at least in part on the size of the left atrial appendage to which it is applied.

Moreover, in at least one preferred embodiment, one end of the one single strand of occlusion material may be fixedly connected to the distal end portion and movable therewith into aligned, communicating relation with the interior of the left atrial appendage. This will prevent an inadvertent puncture or penetration of a loose or free end of the single strand into the wall tissue of the corresponding left atrial appendage being treated. As a result and as emphasized in greater detail herein, each progressively formed array disposed within the interiors of the left atrial appendage of different patients will be effectively "arbitrary" in size, dimension, disposition, etc.

Additional features of the delivery instrument, specifically including the distal end portion is its structural and operative features which enable it to be used as a closure structure. Therefore, when aligned and/or disposed in communication with the interior of the appendage, the distal end portion may be disposed in covering, closing relation to the entrance to the left arterial appendage in a secure manner. As a result, the progressively formed arbitrarily intermingled array of occlusion material, as well as any blood clot interacting therewith, will be prevented from exiting the left atrial appendage but will remain therein. Further, the distal end and/or closure structure may be selectively disposed into a closing orientation. The closing orientation may be more specifically defined by a radially outward expansion thereof into an increased dimension and configuration which facilitates the closing and/or covering of the appendage entrance. When so disposed, the distal end portion and/or closure structure defined thereby may be disconnected from a remainder of the delivery instrument. Thereafter, the remainder of the delivery instrument may be subsequently removed after single strand of occlusion material has been delivered and the occlusion of the left atrial appendage has been accomplished.

Other structural features which may be directly associated with the movable distal end portion and/or cover structure is the provision of the outer face or surface portion formed of a liquid impermeable material such as, but not limited to Dacron® as such, blood and blood flow is prevented from passing through the distal end portion/closure structure once it is disposed and expanded into its closing orientation and further disposed in closing relation to the appendage entrance.

Utilizing the assembly of the present invention as set forth above the intended method for accomplishing left atrial appendage occlusion includes positioning the delivery instrument in communicating relation with the interior of the left atrial appendage and expanding the removable distal end portion or cover structure associated therewith into a closing orientation. The closing orientation of the cover structure is sufficient to close and/or cover the entrance, wherein an inner extremity of the distal end portion or cover structure is disposed at least partially within the interior of the left atrial appendage. The cover structure is then connected or secured to the appendage entrance and at least one single strand of occlusion material is progressively fed into the interior of the left atrial appendage. In doing so, the arbitrarily intermingled array of occlusion material is progressively formed until a sufficient quantity or length of the one single strand is disposed within the interior of the appendage and is of sufficient size and shape to correspond to the interior dimension and configuration of the left atrial appendage. As a result, any pooling of blood within the interior of the appendage will interact with the arbitrarily intermingled array of occlusion material, such that any clotting of blood will be directly associated with the occlusion material itself.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIGS. 7A and 7B are sequential steps in the attendant method of the present invention, wherein at least one single strand of occlusion material is progressively delivered into the interior of the left atrial appendage and the formation thereof into an arbitrarily intermingled array which accomplishes the intended occlusion.

FIG. 10 is a longitudinal sectional view of the embodiment of FIG. 9 when in a cover structure thereof is in a collapsed orientation.

FIG. 11 is a longitudinal sectional view of the embodiment of FIGS. 9 and 10 wherein the cover structure is in an expanded orientation.

Like reference numerals refer to like parts throughout the several views of the drawings.

DETAILED DESCRIPTION OF THE PREFERRED EMBODIMENT

The present invention is directed to an instrument assembly and attendant method for accomplishing the occlusion of a left atrial appendage as schematically and collectively represented in the accompanying Figures.

Figure 1:
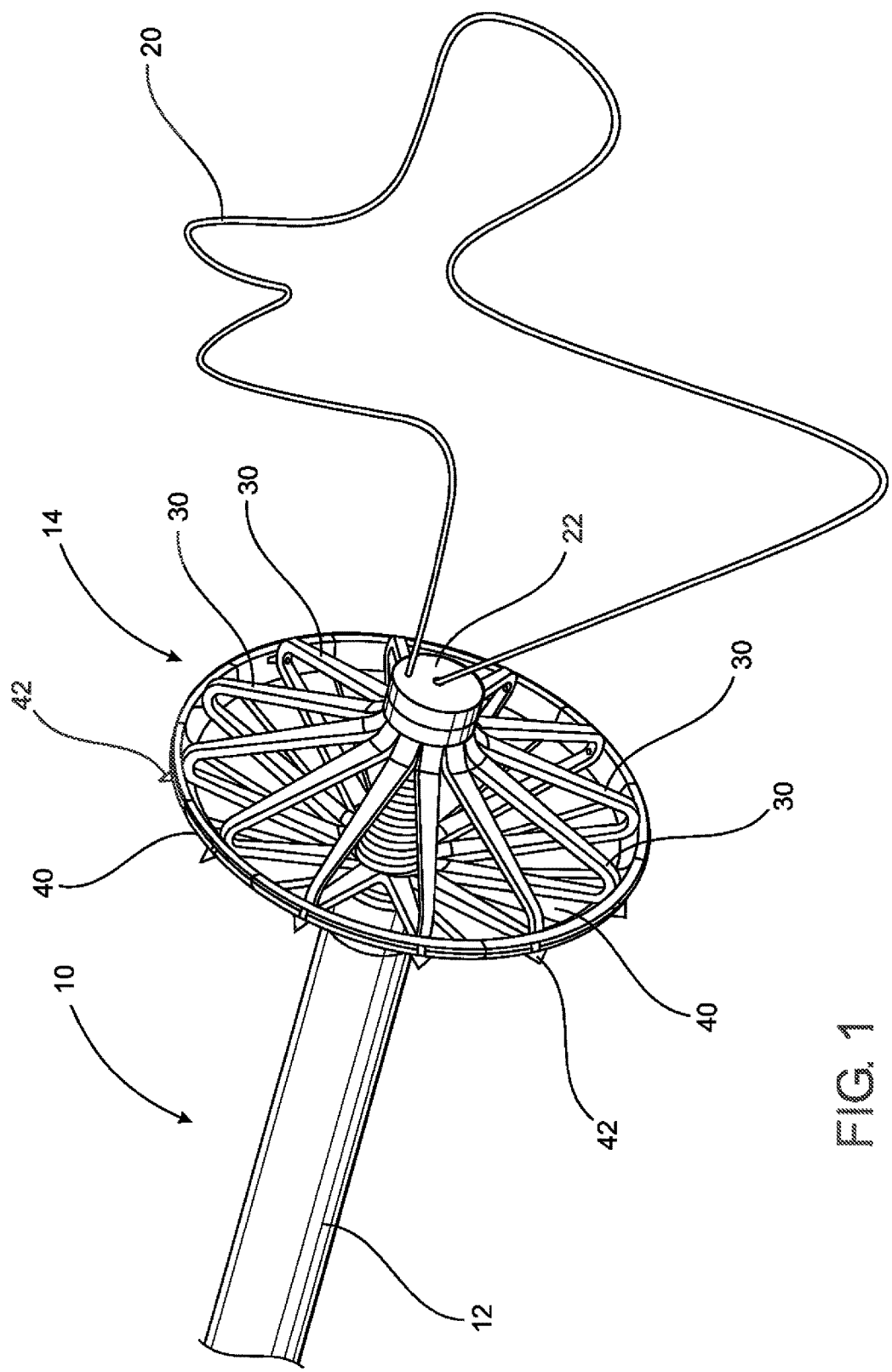
FIG. 1 is a perspective view in partial cutaway of one preferred embodiment of a delivery instrument of the present invention structured for performing the occlusion of the left atrial appendage of the human heart.
Figure 2:
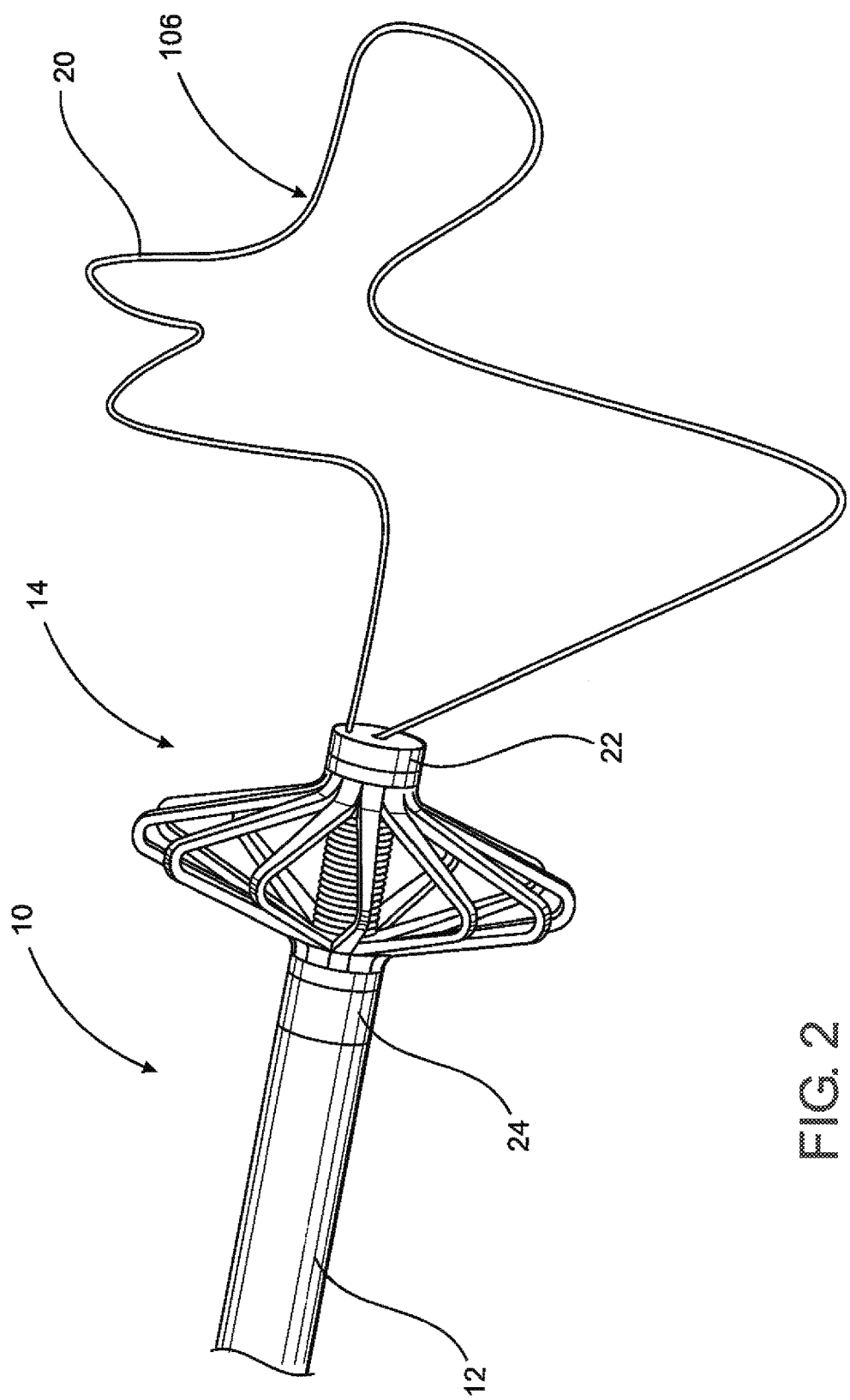
FIG. 2 is a perspective view in partial cutaway of another embodiment of the delivery instrument similar in operation to the embodiment of FIG. 1.
Figure 3:
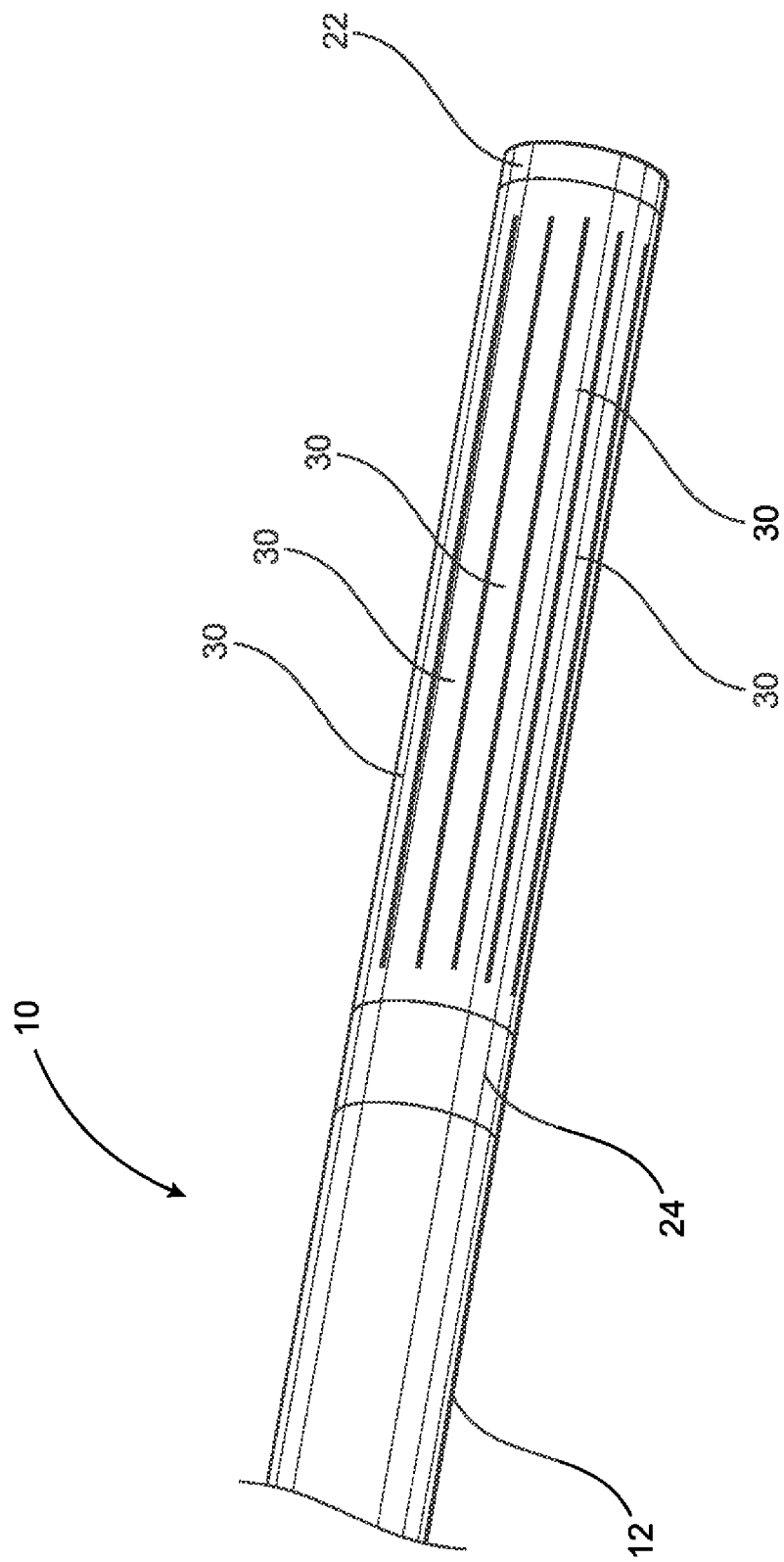
FIG. 3 is a perspective view in partial cutaway of the delivery instrument in a contracted orientation which facilitates entry into the heart and access to the left atrial appendage.
Figure 4:
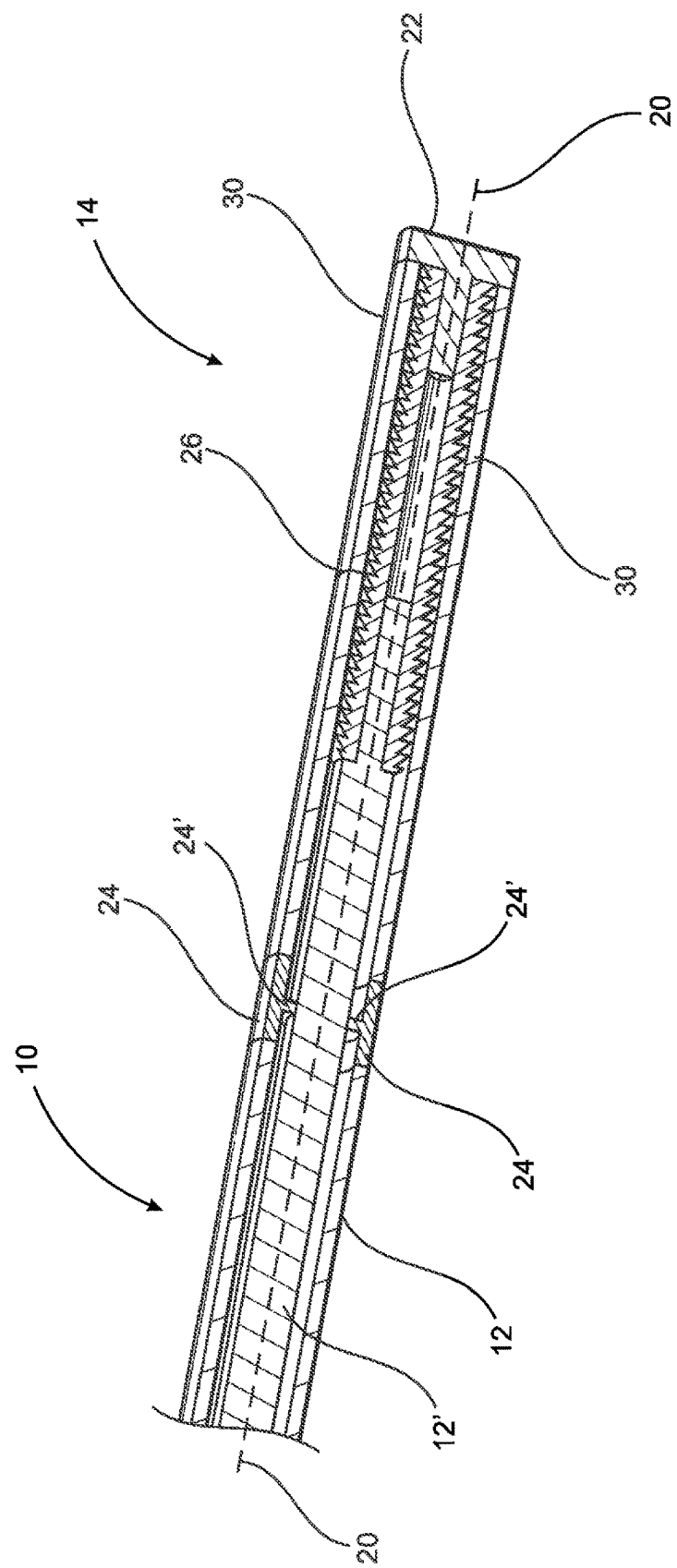
FIG. 4 is a perspective view in partial cutaway and interior section of the embodiment of FIG. 3.
Figure 5:
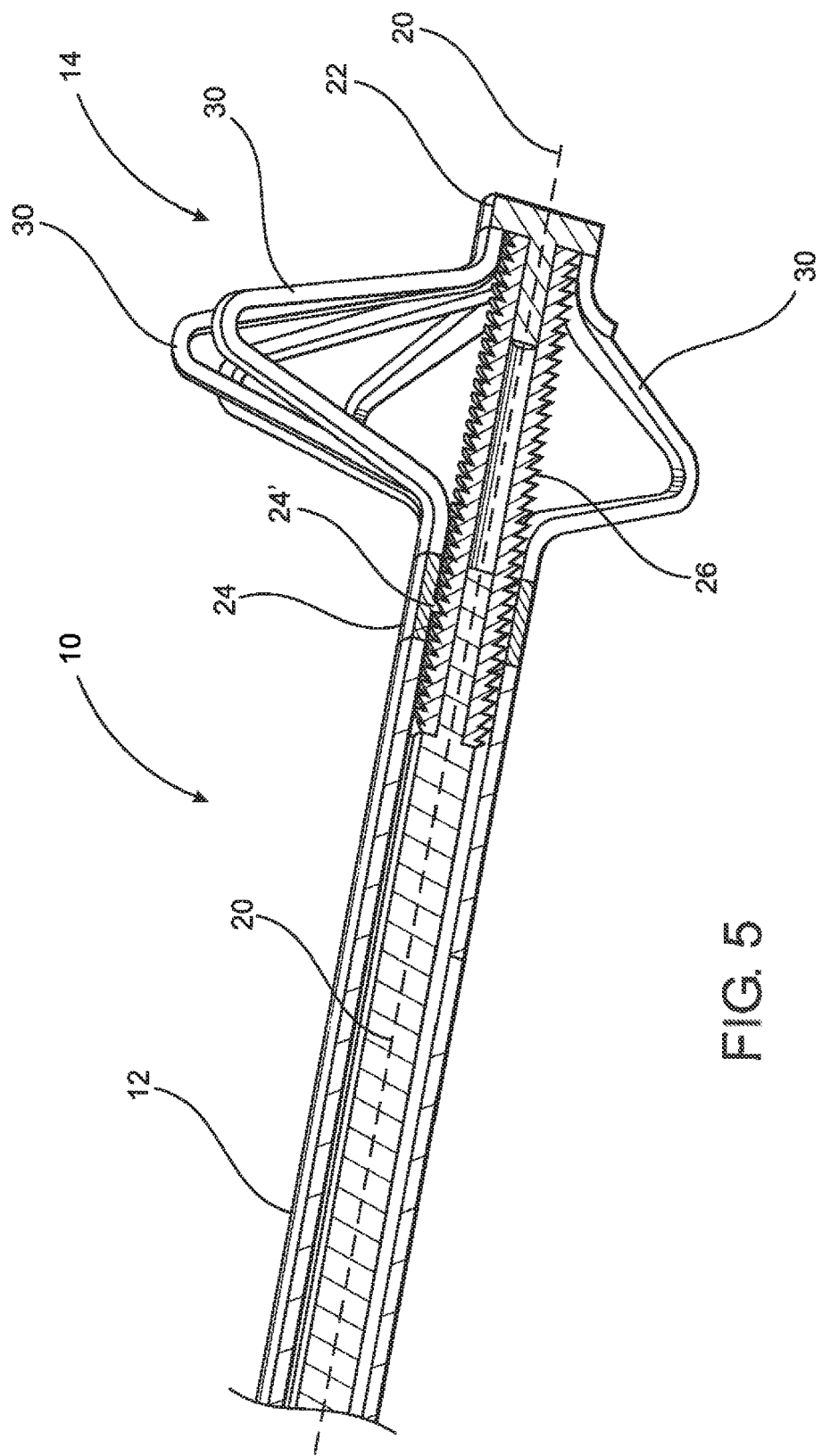
FIG. 5 is a perspective view in partial cutaway and interior section of the embodiment of FIGS. 3 and 4 representing the distal end portion of the delivery instrument in an expanded orientation.
Figure 6:
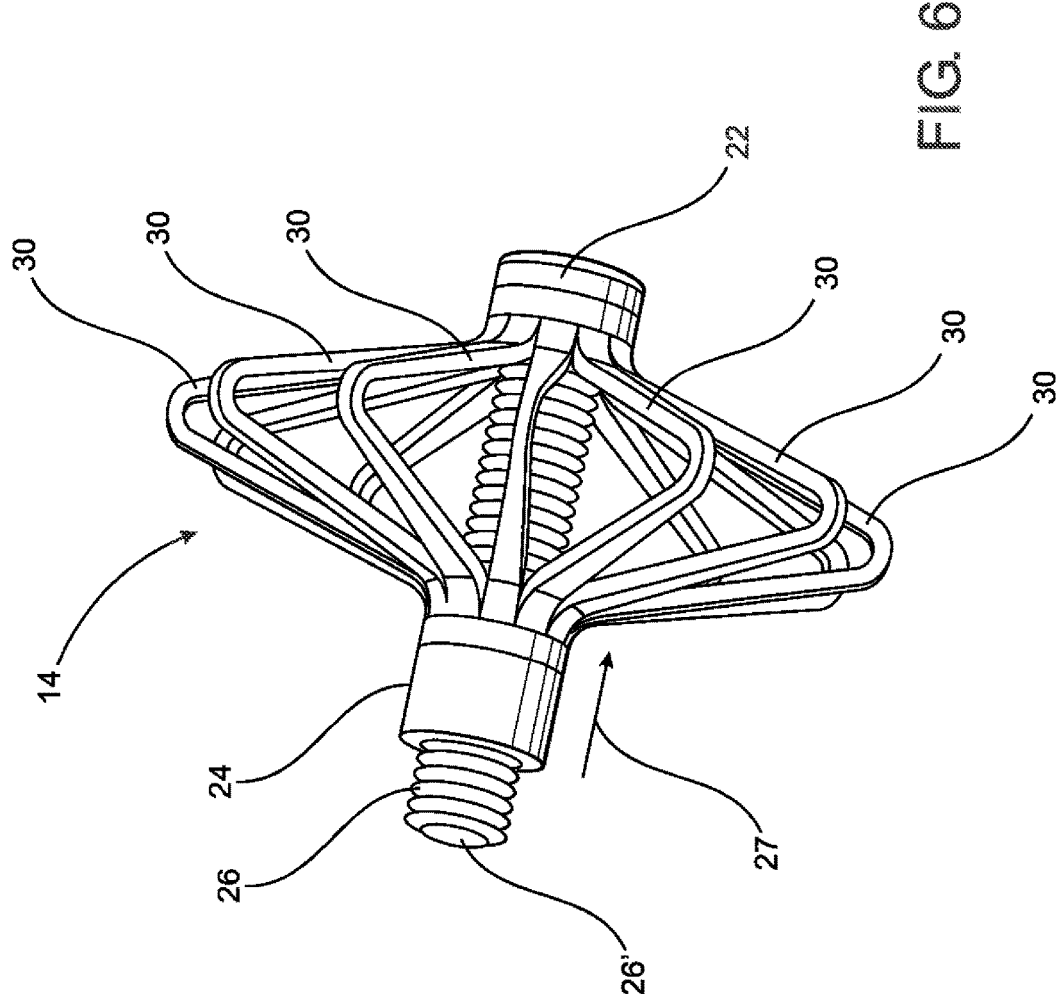
FIG. 6 is a perspective view of the distal end portion of the embodiment of FIGS. 1, 2, and 5 wherein the distal end portion is disconnected from the remainder of the delivery instrument and is disposed in the expanded orientation.

More specifically with primary reference to FIGS. 1 and 2, one or more preferred embodiments of the present invention include a delivery instrument generally indicated as 10, which may include an elongated catheter, or delivery tube 12. The delivery catheter 12 includes an interior lumen or channel as schematically represented in FIGS. 4 and 5 and described in greater detail herein. The delivery instrument 10 also includes a distal end portion generally indicated as 14 movable with the delivery catheter 12 and selectively removable therefrom. As such, the distal end portion 14 is positioned in aligned and communicating relation with the entrance 100 and the interior 102 of the left atrial appendage, generally and schematically represented as 104 in FIGS. 7A and 7B. The distal end portion 14 may also define a cover structure for closing and/or covering the entrance 100 of the interior 102 of the left atrial appendage 104, when properly disposed into an expanded orientation or closing orientation, as represented in FIGS. 1, 2, 5, 6, 7a and 7B.

Therefore, when in the expanded orientation, the distal end portion or cover structure 14 facilitates the delivery of the single strand 20 of occlusion material, generally indicated as 106, into the interior 102 of the appendage 104, from the delivery instrument 10. As represented, the occlusion material comprises at least one single strand 20 or a plurality of single strands (not shown). In either application, the at least one single strand 20 is movably mounted on and connected to the delivery instrument 10, and is disposable outwardly from the delivery instrument 10. More specifically the at least one single strand 20 is disposable outwardly from the distal end portion or cover structure 14, such as through the distal extremity 22 thereof, into the interior 102 of the left atrial appendage 104. Moreover in the various preferred embodiments of the present invention, the at least one single strand 20 of occlusion material may have at least a portion of its length initially stored and movable within the interior of the delivery catheter or tube 12. A supply of such occlusion material may be mounted on and/or otherwise operatively associated with the delivery instrument 10. Accordingly, the at least one single strand is "progressively" fed or delivered outwardly from the delivery instrument 10 preferably through the interior thereof and through the interior of the distal end portion 14, into the interior 102 of the left atrial appendage 104.

Additional structural features of the delivery instrument 10, specifically includes the distal end portion or cover structure 14, being removably attached to a corresponding end of the delivery catheter 12, such as by a removable hub as at 24. It is emphasized that the delivery instrument 10, as well as the distal end portion or cover structure 14, may assume a variety of different structural and operative features which facilitate the delivery of the occlusion material 106, in the form of the at least one single strand of flexible material 20, progressively into the interior 102 of the left atrial appendage 104. As shown in FIGS. 4 and 5, a threaded linkage assembly, generally indicated as 26, is directly associated with the distal end portion 14. As such, the threaded linkage 26 is operatively structured to interact with interior portions of the delivery tube or catheter 12, such as at member 24'. As such, rotation of the interior rod 12' will serve to rotate the threaded linkage 26 through interaction with the thread member 24'. This in turn will cause an outward, radial expansion of the distal end portion 14 into what may be referred to as the aforementioned expanded orientation or closing orientation as it is disposed in covering or closing relation to the entrance 100 of the interior 102 of the left atrial appendage 104.

Therefore, the associated hub 24 may include internal threads or other features which, when rotated, will force a longitudinal movement of the hub 24 along the threaded linkage 26 as schematically represented by directional arrow 27. Such longitudinal movement of the connecting hub 24 towards the distal extremity 22 of the distal end portion 14 will cause an outward, radial expansion of a plurality of flexible material ribs 30, which collectively define the side wall portions of the distal end portion 14. The flexibility of the ribs 30 is demonstrated by the different positions or orientations thereof such as when the distal end portion 14 is connected to the corresponding end of the delivery tube or catheter 12 in its compacted orientation prior to expansion. In addition, the end or extremity 26' of the threaded linkage 26 may also be structured to facilitate the detachment or disconnection of the distal end portion 14 from the remainder of the delivery instrument 10 and/or delivery catheter 12 through appropriate manipulation of the remainder of the delivery instrument 10 as should be apparent.

It is of further note that the structure of the distal end portion or cover structure 14 may vary significantly in facilitating the selective positioning into its expanded orientation or closing orientation in order to facilitate it covering or closing the entrance 100 of the left atrial appendage 104. It is to be further noted that the size and/or configuration of the distal end portion and/or cover structure 14 may vary at least partially based on the degree of outward or radial expansion. The variances in circumferential and/or diametrical dimension facilitate the proper sizing and positioning of the distal end portion or cover structure 14 into covering or closing relation to the entrance 100, as schematically represented in FIGS. 7A and 7B. As also represented throughout the Figures, the delivery instrument 10, specifically including both the delivery catheter 12 and the distal end portion 14, may be further structured to accommodate the passage of the single strand 20 of occlusion material through the interior of the delivery tube or catheter 12 and through the interior of the distal end portion 14 out of the distal extremity 22 of the distal end portion 14.

With primary reference to FIGS. 1 and 2, the distal end portion or cover structure 14 may include an outer face 40 which is formed from a liquid impermeable material such as, but not limited to, Dacron™. As such, the outer face 40 serves to restrict the flow of fluid between the left atrium and the interior 102 of the left atrial appendage 104. Similarly, the exterior face 40, as well as the structure of the plurality of side ribs 30, serve to restrict the migration of any blood or blood clot from the interior 102 of the left atrial appendage 104, especially due to the fact that a pooling of blood or resultant blood clot will intermix or interact with the occlusion material 106. As used herein, the term exterior face 40 is descriptive of the location of the liquid impermeable face 40 within the interior of the atrium but substantially or entirely excluded from the interior 102 of the left atrial appendage 104.

Further with regard to FIG. 1, the distal end portion or cover structure 14 may also include one or more gripping members 42 preferably, but not exclusively, disposed about the outer periphery of the distal end portion 14 and/or exterior face 40. The disposition and structure of the gripping members 42 is such as to facilitate a secure, fixed attachment such as by, but not limited to, penetration of the distal end portion and/or cover structure 14 in its closing or covering relation to the entrance 100 of the left atrial appendage 104. Gripping engagement and/or interaction of the gripping member 42 are also schematically represented in FIGS. 7A and 7B.

Figure 8A:
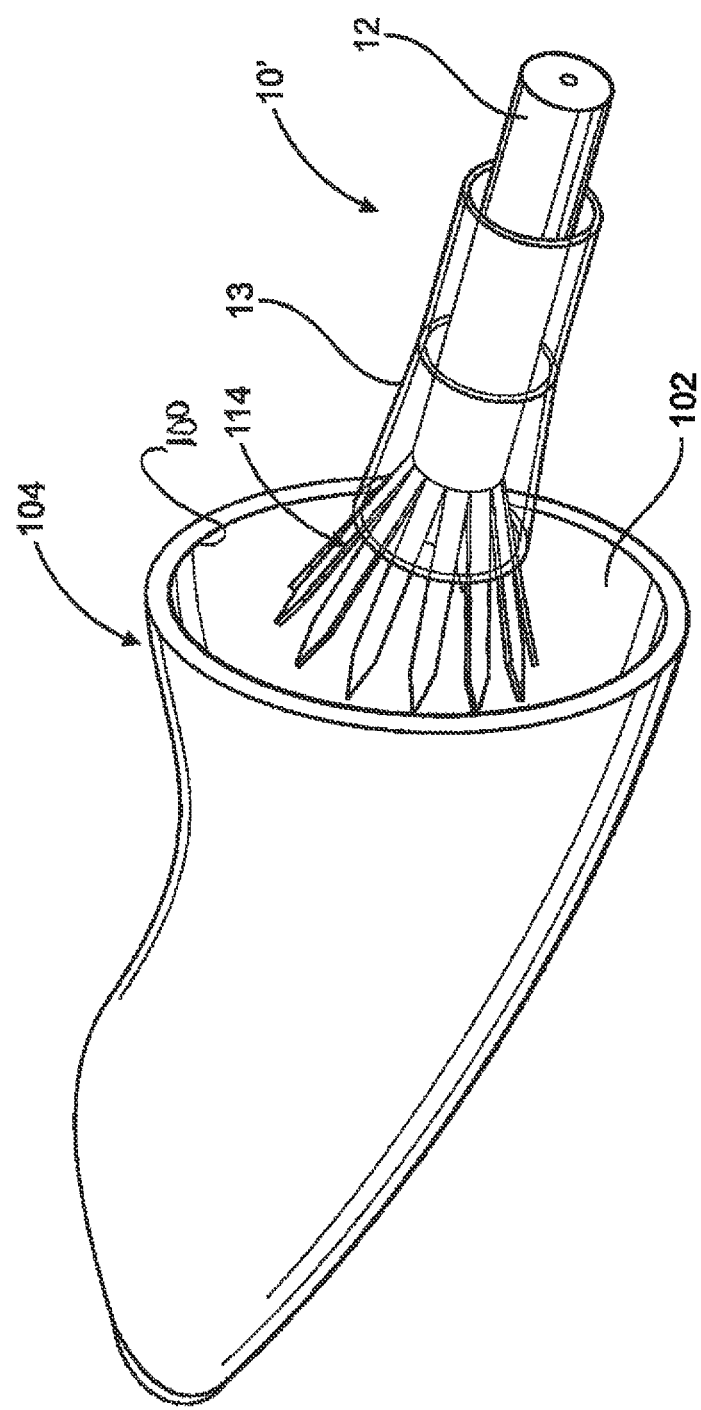
FIGS. 8A-8C are perspective schematic views in partial cutaway representing successive positioning of another embodiment of a cover structure of the present invention in closing relation to the interior of the left atrial appendage.
Figure 8B:
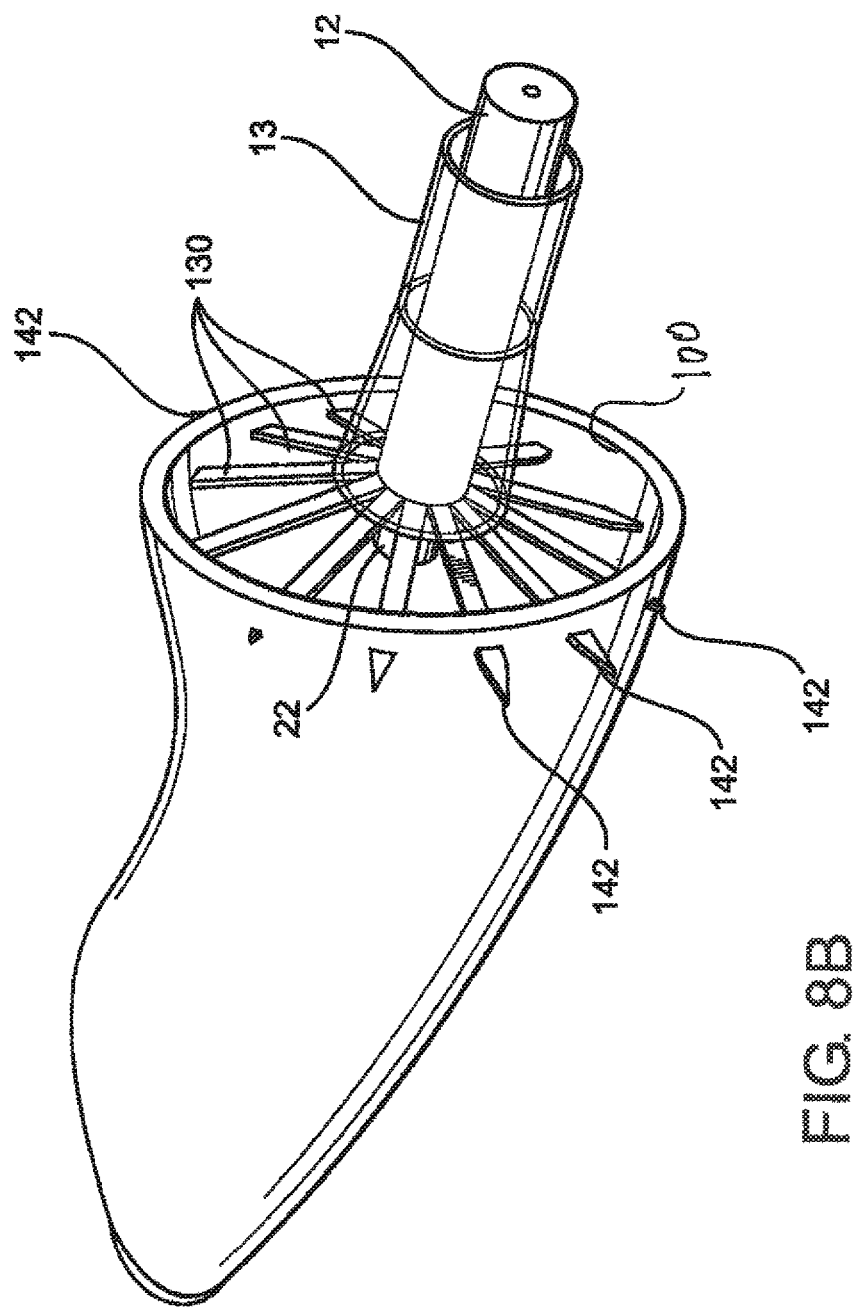
Figure 8C:
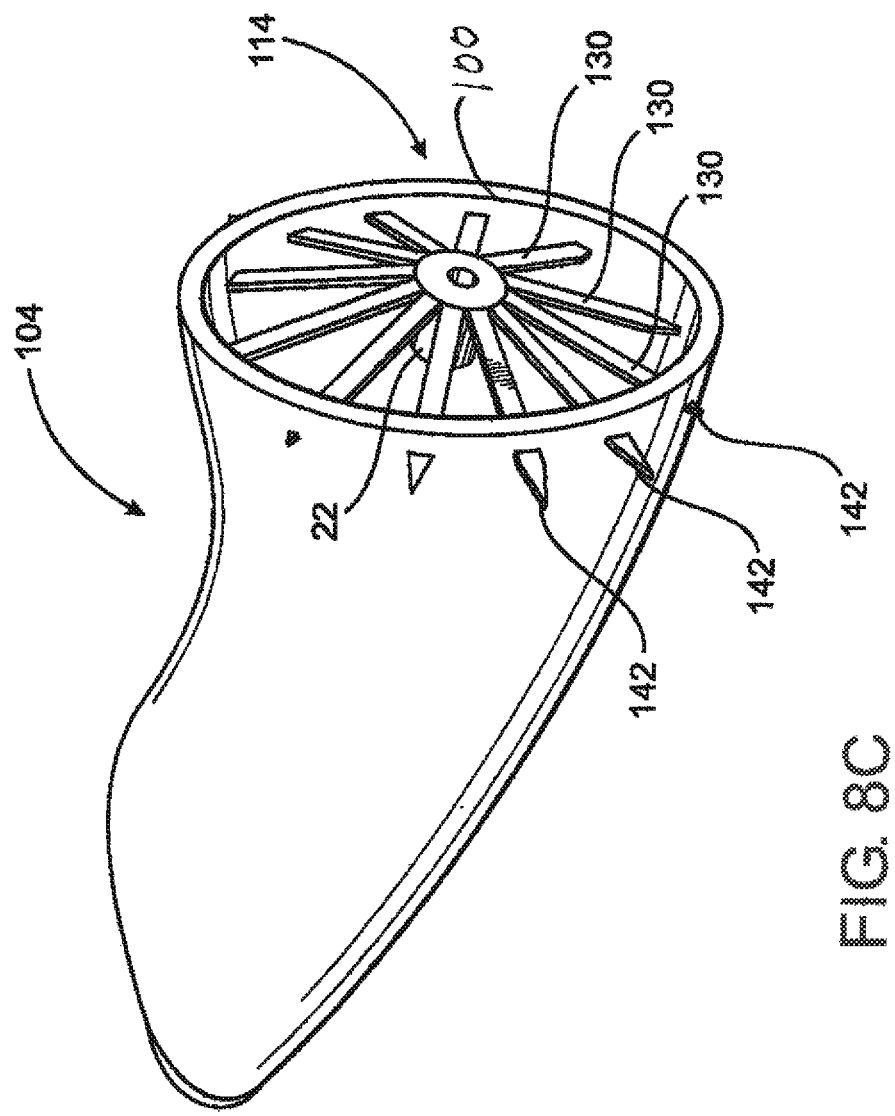
Figure 9:
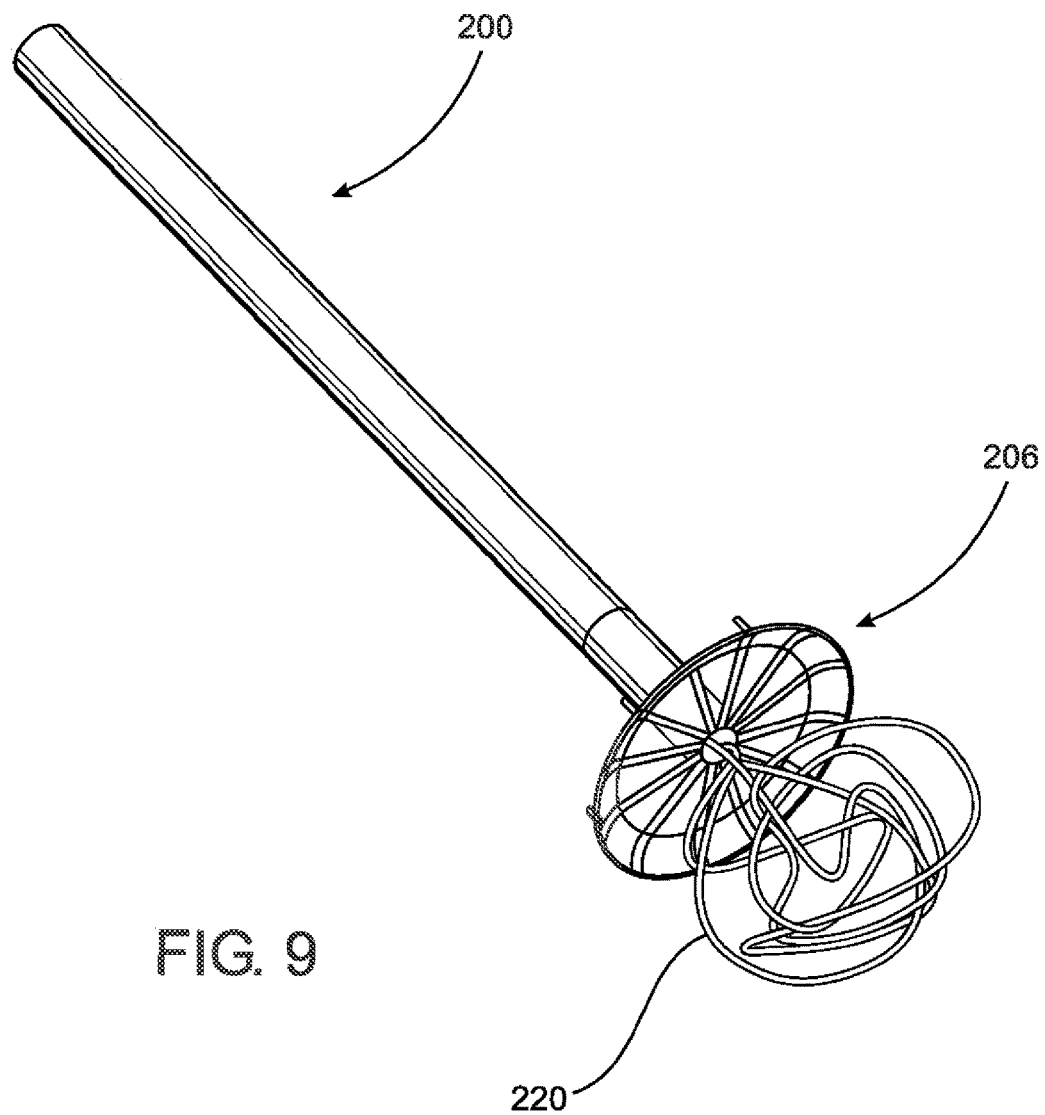
FIG. 9 is a perspective view of yet another preferred embodiment of the present invention.

Yet another embodiment of the present invention includes a structural and operative variation of the cover structure and is generally represented as 114 in FIG. 8A-8C. More specifically, the cover structure 114 comprises a plurality of ribs 130 structured and initially disposed to move with and relative to the delivery tube or catheter 12. Moreover, the ribs 130 may be extended out of the distal end of the delivery tube 12 and through an outer sheath or like structure 13 into a radially expanded position and closing orientation relative to the entrance 100 to the interior 104 of the left atrial appendage 102, as represented in FIGS. 8A and 8B. Although not shown in FIGS. 8A-8C, Dacron or other appropriate material 40 may be used on or at least partially define the outer face of the cover structure 114, as described with references to the embodiment of FIG. 1.

Moreover, each or at least some of the ribs 130 include a pointed or other appropriately configured outer end 142 which engages and connects, such as by penetration, to the tissue substantially comprising the outer periphery of the entrance 100 of the left atrial appendage 102. Such positioning of the outer ends 142 will maintain the cover structure 114 in the expanded orientation and closing relation to the entrance 100 of the interior 102 as represented in FIGS. 8B and 8C. Once so positioned and after the single strand 20 of occlusion material 106 has been progressively passed into the interior 102 in the form of the arbitrarily intermingled array 110, the remainder of the delivery instrument 10' and catheter 12 are detached from the cover structure 114 and removed from the site.

With primary reference to FIGS. 7A and 7B, the occlusion material in one or more preferred embodiments of the present invention comprises the at least one single strand 20 of elongated, flexible material. The material from which the single strand 20 is formed may include, but not be limited to, a nitinol wire or chord. While the progressive feeding of the at least one single strand 20 into the interior 102 of the left atrial appendage 104 is described with reference to and in terms of the structure of the embodiment of FIGS. 1-6, the described procedure and/or method is substantially the when the embodiment of FIGS. 8A-8C are used. The cooperative disposition and structure of the at least one single strand relative to the delivery instrument 10, delivery tube or catheter 12 and distal end portion 14 facilitates a portion of the length of the one single strand 20 being movable preferably through an interior of the delivery instrument 10, as schematically represented in FIGS. 4 and 5. Similarly, the length of the single strand 20 is movable through and outwardly from the distal end portion and/or cover structure 14 into the interior 102 of the left atrial appendage 104. More specifically, at least a portion of the length of the at least one single strand 20 of occlusion material 106 is movably disposed on or within the delivery instrument and is progressively movable through the distal end or cover structure 14, as it is fed into the interior 102 of the left atrial appendage 104.

Upon entry and due at least in part to the flexibility as well as the progressive feeding or passage of the one single strand 20, it will progressively form into an "arbitrarily intermingled array" 110 of the occlusion material 106 as clearly represented in FIG. 7B. As should be apparent, once the distal end portion and/or closure structure 14 is in the covering or closing relation to the entrance 100, as in FIGS. 7A and 7B, the delivery instrument 10 may be selectively manipulated so as to force movement or passage of the one single strand 20 of occlusion material into the interior 102. Further, as demonstrated in FIG. 7B as additional amounts or lengths of the single strand 20 enters the appendage interior 102 the "arbitrarily intermingled array" 110 of the interiorly collected occlusion material 106 will be progressively formed.

It is emphasized that the term "arbitrarily intermingled array" 110 when describing the occlusion material 106, may serve to accurately describe the various portions of the length of the single strand 20 being folded, looped, curled, intermingled, etc. about itself as the interior 102 of the appendage 104 begins to fill, as schematically and successively represented in FIGS. 7A and 7B. Therefore, the rotation and/or position of the various portions of the length of the single strand 20 within the appendage interior 102 will be "inconsistently" arranged and therefore "arbitrarily intermingled" or intermixed with one another, when the occlusion material 106 is applied to different left atrial appendages 104 of different patients. It is further emphasized that in one or more preferred embodiments, the various portions of the length of the single strand 20 will form the arbitrary intermingled array 110 and will not necessarily be connected or attached to one another and not connected or attached to the tissue portions within the left atrial appendage 104. Therefore and as indicated above, due at least in part to the flexibility as well as the progressive entry of the at least one single strand 20 into the appendage interior 102, the at least one single strand 20 will form differently shaped and dimensioned "arrays" 110 of occlusion material 106, as the various portions of the length of the one single strand 20 are intermixed in folding, overlapping, curled, etc. relation to one another.

As schematically represented, the arbitrarily intermingled array 110 of occlusion material 106 may have different dimensions and/or configurations depending at least in part on the size of the interior 102 of the left atrial appendage 104 to which it is applied. In at least one preferred embodiment of the present invention, the arbitrarily intermingled array 110 is dimensioned and configured to fill at least a majority of the interior 102 of the appendage 104 and/or substantially fill the entirety thereof. When so filled, the arbitrarily intermingled array 110 will substantially conform or correspond to the interior configuration of the left atrial appendage 104, in the manner clearly represented in FIG. 7B.

This partial filling or complete filling will thereby serve to accomplish an intended interaction of any blood pooling within the interior 102 of the appendage 104. Moreover, the blood will interact with the arbitrarily intermingled array 110 of occlusion material 106 in a manner which will maintain at least minimal blood circulation and avoid revascularization.

Additional features of the formed arbitrarily intermingled array 110 of occlusion material 106 is the attachment of the proximal end 20' to the distal extremity 22 of the distal end portion or cover structure 14. This connection will prevent inadvertent penetration or puncturing of the interior wall tissue of the left atrial appendage 104. Further, upon completion of the formation of the arbitrarily intermingled array 110 of occlusion material 106 within the interior 102 of the left atrial appendage 104, the remainder of the delivery instrument 110, such as the delivery tube or catheter 12 is detached from the corresponding end or hub 24 and/or the extremity 26' of the linkage 26 and removed from the interior of the heart. As such, the opposite or distal end 20" of the at least one single strand 20 of occlusion material 106 will remain attached to the distal end portion or cover structure 14.

Yet another preferred embodiment of the assembly for performing an occlusion of the left atrial appendage is represented in detail in FIGS. 9 through 17. More specifically, a delivery instrument is generally indicated as 200 and includes an introduction member 202 structured for introduction or passage into the heart in an operative position. The operative position of the delivery instrument 200 comprises its direct communicating relation with the left atrial appendage, such as schematically represented with regard to the description of the different embodiments of FIGS. 7A, 7B and 8A-8C.

Figure 10A:
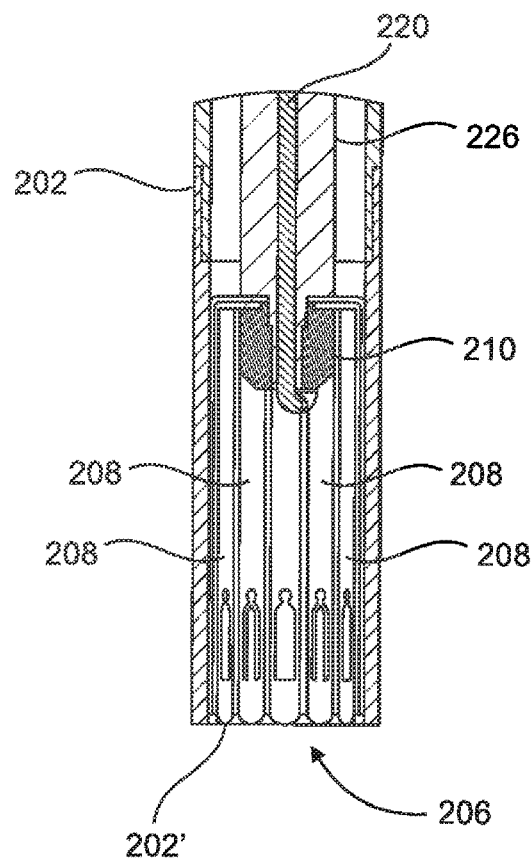
FIG. 10A is a detailed view of a gripping member portion of FIG. 10.
Figure 16:
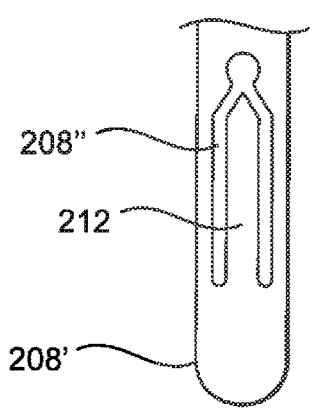
FIG. 16 is a detailed view in partial cutaway of the distal end of one of a plurality of ribs associated with the cover structure of the embodiment of FIGS. 1 through 15, when the cover structure is in a collapsed orientation.

In addition, the delivery instrument 200 includes a positioning member 204 initially disposed telescopically within the interior of the introduction member 202 so as to be movable relative thereto. A cover structure 206 is initially connected to the distal end of the positioning member 204 so as to move therewith between an expanded orientation of FIGS. 11 through 15 and a collapsed orientation as represented in FIGS. 10 and 10A. As will be described in greater detail hereinafter, the cover structure 206 is removably connected to the positioning member 204 so as to be detached therefrom when the cover structure 206 is operatively disposed in closing relation to the entrance of the left atrial appendage 104, as schematically represented in FIG. 7B with regard to the above described embodiment and as also represented at least schematically in FIG. 13.

The selective detachment of the cover structure 206 from the positioning member 204 may be accomplished by an appropriate linkage or connector 226 which may be structurally and/or operatively similar to the connecting linkage 26 associated with the embodiments of FIGS. 1 through 6. It is emphasized that other connecting linkage may be utilized to facilitate the accurate position of the cover structure 206, when in the collapsed orientation of FIGS. 10 and 10A, as well as the detachment of the delivery instrument 200 there from, when the cover structure 206 is operatively disposed in the aforementioned covering relation to the entrance and interior of the left atrial appendage 104. As clearly represented in FIGS. 12 through 15, the cover structure 206 includes a plurality of ribs 208 each formed of a material having sufficient flexibility to provide an "inherent bias" thereto, which facilitates their "automatic" disposition from the collapsed orientation of FIGS. 10 and 10A into the expanded orientation of FIGS. 11 through 15.

Accordingly, the collapsed orientation of the cover structure 206 comprises the plurality of ribs 208 being disposed in substantially longitudinal alignment with one another and with the length and/or central axis of the delivery instrument 200. However, upon disposition of the cover structure 206 through the open end 202' of the introduction member 202 the inherent bias associated with each of the plurality of ribs will force them into the expanded orientation comprising a radially outward, spaced apart orientation as represented throughout FIGS. 11 through 15. Additional features of the cover structure 206 include a central hub 210 interconnected to and disposed in interconnecting relation with each of the plurality of flexible material ribs 208. Therefore, the aforementioned expanded orientation of the cover member 206 may be further defined by the plurality of ribs 208 extending radially outward from the hub 210 in spaced apart orientation as clearly represented in FIG. 15.

Features of the cover structure 206 comprise the inclusion of the plurality of gripping members 212 connected to free or outer distal ends 208' of at least some of the plurality of ribs 208. With primary reference to FIGS. 16 and 17, the gripping members 212 may have a pointed or other appropriate configuration to facilitate the penetration of the left atrial appendage 104 in an area adjacent to the entrance thereof as also schematically represented in the embodiments of FIGS. 8A through 8C. Further, each of the gripping members 212 is formed of a material having sufficient flexibility to also include the aforementioned "inherent bias". Accordingly, when each of the plurality of ribs 208 are in the collapsed orientation on the interior of the introduction member 202, the plurality of gripping members 212 are substantially coplanar or at least longitudinally aligned with the remainder of the corresponding ones of the distal ends 208' as clearly represented in FIGS. 10A and 16. Moreover, corresponding ones of the distal ends 208' may have an at least partially apertured construction as at 208" wherein the gripping members 212 are disposed within the interior of the corresponding opening or aperture, as at 208'" when the cover structure 206 is in the collapsed orientation.

Figure 17:
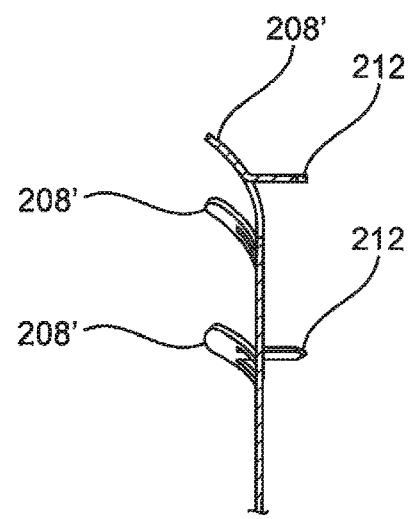
FIG. 17 is a sectional view in partial cutaway of one distal end of one of a plurality of ribs and an included gripping member connected thereto when the cover structure is in an expanded orientation.
Figure 12:
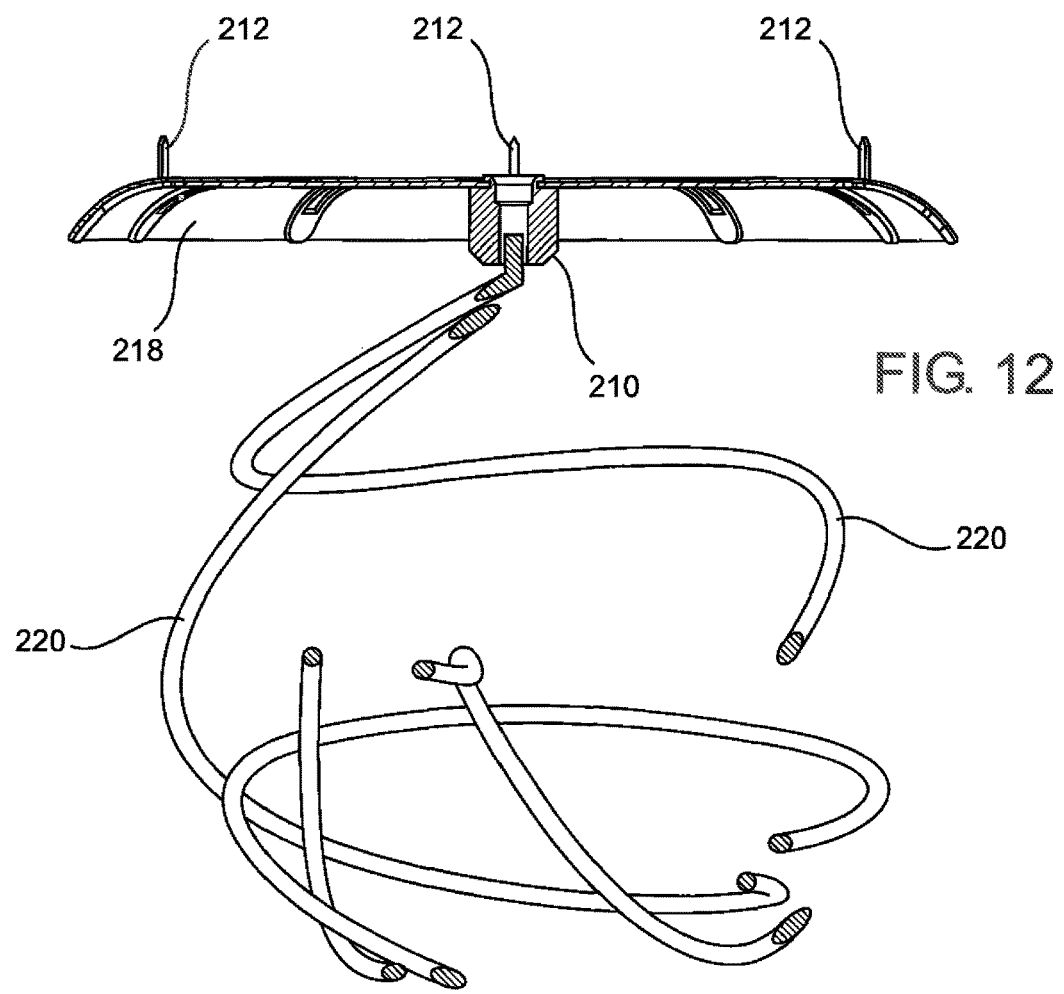
FIG. 12 is a transverse sectional view and partial cutaway of the cover structure of the embodiments of FIGS. 9 through 11 in an expanded orientation wherein occlusion material associated therewith is dispensed therefrom.

However, due to the aforementioned inherent bias, once the ribs pass out through the opening 202' into the expanded orientation of FIGS. 11 through 15, the plurality of gripping members 212 will extend transversely outward from the corresponding distal end 208'. In addition, each of the plurality of distal ends 208', whether directly associated with a gripping member 212 or not, are structured to have an at least partially curvilinear configuration as clearly represented in FIG. 17. Therefore, the inherent bias integrated into each of the plurality of ribs 208, as well as the distal ends 208' and the gripping members 212, will facilitate the "automatic" assumption of the configuration of the gripping members 212 and each of the distal ends 208' as represented in FIG. 17. As will be explained in greater detail hereinafter, each of the plurality of gripping members 212 extend transversely outward from the outer side 213 of the cover structure 206, wherein the inner or interior side 215 of the cover structure 206 faces inwardly towards the interior of the left atrial appendage 104 when the cover structure 206 is disposed in the expanded orientation and in covering relation to the entrance to the left atrial appendage 104, similar to the schematic representation of FIGS. 7A and 7B.

Other structural features of the cover structure 206 include a facing material or structure 218 disposed in covering relation to the plurality of ribs when in either the expanded or the collapsed orientations, as described above. Moreover, the facing material 218 includes the outer side 213 and the inner side 215 and may be formed of a Dacron® or other flexible and liquid impermeable material. The flexibility of the facing material 218 facilitates its movement in connected, covering relation to the plurality of ribs 208 as they move and/or are positioned between the collapsed and the expanded orientations.

Similar to the embodiment of FIGS. 1 through 7, and again with at least partial reference to the schematic representations of FIGS. 7A and 7B, the delivery instrument 200 is structured to dispense at least one single strand of occlusion material 220 into the interior 102 of the left atrial appendage. The occlusion material 220 is progressively dispensed or fed through the cover structure 206 and more specifically through the opening 210' of the hub 210 into the interior 102 of the left atrial appendage 104. Accordingly, the occlusion material 220 comprises at least one single strand of elongated flexible material such as, but not limited to, nitinol wire or chord. As applied, the length of the single strand of occlusion material 220 is progressively fed from the interior of the delivery instrument 200 and more specifically from the interior of the positioning members 204 through the hub 210. Moreover, a sufficient length of the occlusion material 220 is continuously and progressively fed into the interior 102 until at least a majority and/or substantially the entirety of the interior 102 is filled. Upon entry and due at least in part to the flexibility and the quantity of the single strand of occlusion material 220 as well as the progressively feeding or passage thereof to the interior 102, the single strand of occlusion material 220 will progressively form into an "arbitrarily intermingled array". Such introduction or dispensing of the single strand of occlusion material 220 is accomplished while the cover structure 206 is in the aforementioned covering relation to the entrance of the interior 102 of the left atrial appendage 104.

Figure 13:
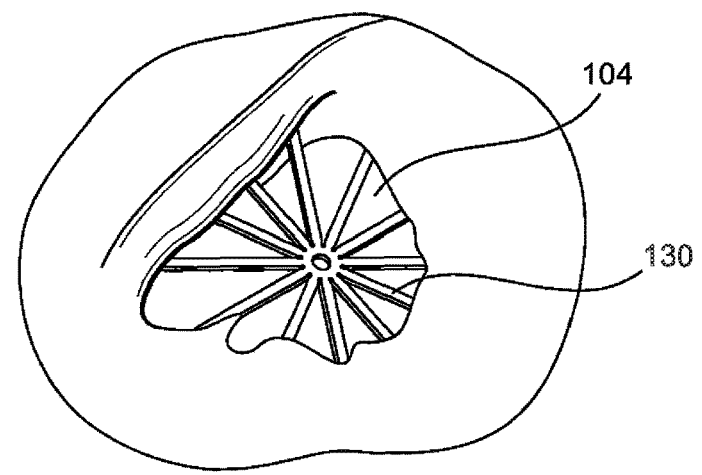
FIG. 13 is a perspective view of the cover structure of the present invention in a covering relation to the entrance of the left atrial appendage wherein cover structure is in conformance with the peripheral configuration of the entrance.
Figure 14:
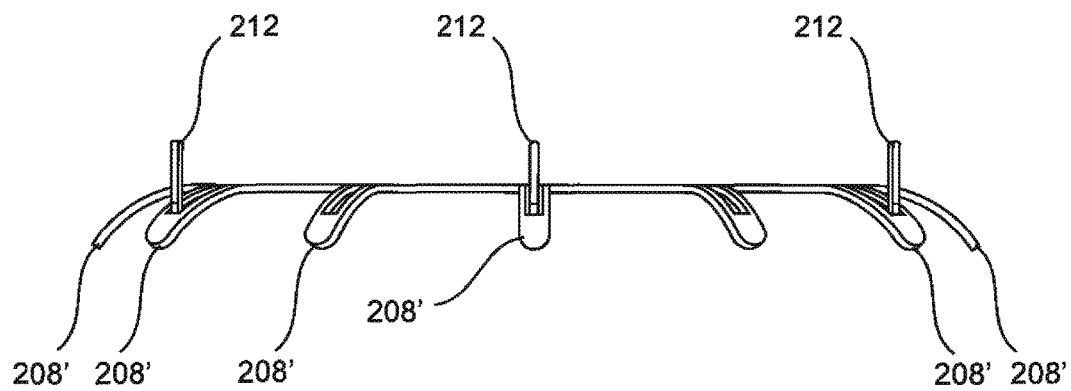
FIG. 14 is an end view of the cover structure of the embodiments of FIGS. 9 through 13 in an expanded orientation.
Figure 15:
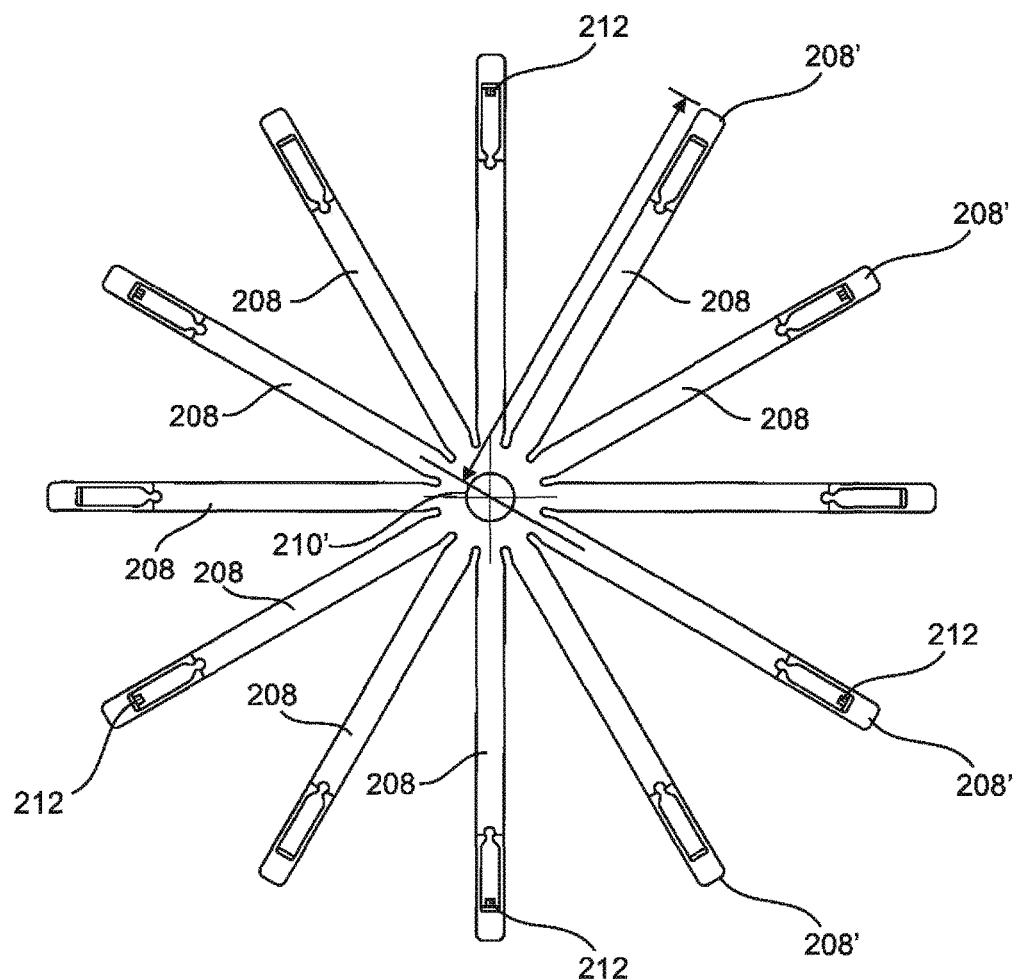
FIG. 15 is a top plan view of the embodiment of FIG. 14.

Additional features of the cover structure 206 specifically, but not exclusively, including the cooperative structural and operative features of the plurality of ribs 208, gripping members 212, etc. include the plurality of ribs being collectively dimensioned and having sufficient flexibility to dispose the plurality of distal ends 208' into connected relation with the tissue of the left atrial appendage immediately adjacent to the entrance thereof. Moreover, the distal ends 208' collectively are disposed to substantially conform to the peripheral configuration of the entrance as generally represented in FIG. 13.

It is recognized by medical personnel familiar with the intended procedure of occluding the left atrial appendage that the entrance thereof has a generally non-symmetrical peripheral configuration. In addition, medical personnel have also termed the peripheral configuration of the entrance of the left atrial appendage to be at least partially or substantially oval. Accordingly, the flexibility and dimensions of the plurality of ribs allow them to substantially conform to the normal or conventional "oval" or other normal or conventional configuration of the periphery of the entrance of the left atrial appendage when disposed in the covering relation thereto as described above.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An assembly structured to perform an occlusion of the left atrial appendage, said assembly comprising:
   a delivery instrument structured for operative disposition in communicating relation with an interior of the left atrial appendage, said delivery instrument including a cover structure removably connected thereto,
   occlusion material comprising at least one elongated strand of flexible material mounted on said delivery instrument,
   said delivery instrument operative for progressive axial dispensing of the length of said at least one strand therefrom into the interior of the left atrial appendage, when said delivery instrument is in said operative disposition,
   a dispensed portion of said at least one strand being of sufficient length and flexibility to at least partially fill and conform to the interior of the left atrial appendage,
   said dispensed portion of said at least one strand being of sufficient length and flexibility to define a progressively formed arbitrarily intermingled array of said occlusion material within the interior of the left atrial appendage,
   said cover structure structurally adapted for disposition in a covering orientation, wherein said covering orientation comprises said cover structure disconnected from said delivery instrument and disposed in covering relation to an entrance to the left atrial appendage,
   said cover structure comprising a plurality of ribs movable between a collapsed orientation and an expanded orientation, at least a majority of said plurality of ribs including a gripping member movably connected to a free distal end thereof,
   said collapsed orientation comprising said gripping members disposed in substantially coplanar relation with a remainder of corresponding ones of said distal ends when within an interior of said delivery instrument,
   said expanded orientation further comprises each of said gripping members biased transversely outward from corresponding ones of said distal ends, when said cover structure is in said expanded orientation,
   wherein said at least one strand forming the arbitrarily intermingled array is not attached to itself along its length and is not attached to tissue portions of the heart corresponding to the left atrial appendage when the cover structure is in said covering orientation, and
   wherein when in the covering orientation, each of said plurality of ribs extend radially outwardly and do not project distally of a distal end of a distal end portion.

2. An assembly as recited in claim 1 wherein said expanded orientation comprises said plurality of ribs extending radially outward from said cover structure into connected relation with the left atrial appendage immediately adjacent a periphery of an entrance thereof.

3. An assembly as recited in claim 2 wherein said collapsed orientation comprises said plurality of ribs disposed within an interior of said delivery instrument in substantially longitudinally aligned relation to one another.

4. An assembly as recited in claim 1 wherein said collapsed orientation comprises said plurality of ribs disposed within an interior of said delivery instrument in substantially aligned relation to a length of said delivery instrument.

5. An assembly as recited in claim 1 wherein said covering orientation further comprises said distal ends of said plurality of ribs collectively disposed in conformance with a peripheral configuration of the entrance of the left atrial appendage.

6. An assembly as recited in claim 1 wherein said cover structure further comprises a facing structure connected to said plurality of ribs in covering relation thereto, said covering orientation further comprising said facing structure structurally adapted to be disposed in covering relation to the entrance of the left atrial appendage.

7. An assembly as recited in claim 6 wherein said facing structure is formed of a flexible, liquid impermeable material movable with said plurality of ribs into and out of said collapsed and expanded orientations.

8. An assembly as recited in claim 1 wherein said gripping members are disposed and configured to at least partially penetrate the left atrial appendage adjacent the entrance thereof.

9. An assembly as recited in claim 1 wherein said gripping members extend transversely outward from an outer side of corresponding ones of said distal ends of said plurality of ribs.

10. An assembly as recited in claim 9 wherein said distal ends comprise a curvilinear configuration extending inwardly towards the interior of said left atrial appendage at least when said cover structure is in said expanded orientation and in covering relation to the entrance of the interior of the left atrial appendage.

11. An assembly as recited in claim 1 wherein said delivery instrument comprises an introduction member and a positioning member disposed within said introduction member, said cover structure connected to said positioning member and movable therewith relative to said introduction member between said collapsed and said expanded orientations.

12. An assembly as recited in claim 11 wherein said cover structure is removably connected to said positioning member and detachable therefrom at least when said cover structure is in said covering orientation.

13. An assembly as recited in claim 1 wherein said cover structure comprises a hub, said plurality of ribs connected to and movable with and relative to said hub between said collapsed and said expanded orientations; said hub cooperatively structured and disposed relative to said at least one strand to facilitate progressive passage of a length of said one strand through said hub, into the interior of the left atrial appendage when said delivery instrument is in said operative disposition and said cover structure is in said covering orientation; said dispensed portion of said at least one strand being of sufficient length and flexibility to define a progressively formed, arbitrarily intermingled array of said occlusion material within the interior of the left atrial appendage.

14. An assembly as recited in claim 1 wherein said covering orientation further comprises free distal ends of said plurality of ribs collectively connected to and disposed in conformance with a peripheral configuration of the entrance of the left atrial appendage.

15. An assembly as recited in claim 1 wherein said covering orientation further comprises at least a portion of said cover structure disposed exteriorly of the entrance of the left atrial appendage.

16. An assembly as recited in claim 1 wherein said at least one strand includes a proximal end and a distal end each remaining connected to said cover structure concurrent to said cover structure disposed in said covering orientation and disconnected from said delivery instrument.

17. An assembly structured to perform an occlusion of the left atrial appendage, said assembly comprising:
a delivery instrument structured for operative disposition in communicating relation with an interior of the left atrial appendage, said delivery instrument including a cover structure removably connected thereto,
occlusion material comprising at least one elongated strand of flexible material mounted on said delivery instrument,
said delivery instrument operative for progressive axial dispensing of the length of said at least one strand therefrom into the interior of the left atrial appendage, when said delivery instrument is in said operative disposition,
a dispensed portion of said at least one strand being of sufficient length and flexibility to define a progressively formed arbitrarily intermingled array of said occlusion material within the interior of the left atrial appendage,
said cover structure structurally adapted to be disposed in a covering orientation, wherein said covering orientation comprises said cover structure disconnected from said delivery instrument and disposed in covering relation to an entrance to the left atrial appendage, said covering orientation comprising at least a portion of said cover structure disposed exteriorly of the entrance of the left atrial appendage,
said at least one strand including a proximal end and a distal end each remaining connected to said cover structure concurrent to said cover structure being in said covering orientation,
said cover structure comprising a plurality of ribs movable between a collapsed orientation and an expanded orientation, at least a majority of said plurality of ribs including a gripping member movably connected to a free distal end thereof,
said collapsed orientation comprising said gripping members disposed in substantially coplanar relation with a remainder of corresponding ones of said distal ends on an interior of said delivery instrument,
said expanded orientation further comprising each of said gripping members biased transversely outward from corresponding ones of said distal ends, when said cover structure is in said expanded orientation, and
wherein said at least one strand forming the arbitrarily intermingled array is not attached to itself along its length and is not attached to tissue portions of the heart corresponding to the left atrial appendage when the cover structure is in said covering orientation, and
wherein when in the covering orientation, each of said plurality of ribs extend radially outwardly and do not project distally of a distal end of a distal end portion.

18. An assembly structured to perform an occlusion of the left atrial appendage, said assembly comprising:
a delivery instrument structured for operative disposition in communicating relation with an interior of the left atrial appendage, said delivery instrument including a cover structure removably connected thereto, occlusion material comprising at least one elongated strand of flexible material mounted on said delivery instrument, said delivery instrument operative for progressive axial dispensing of the length of said at least one strand therefrom into the interior of the left atrial appendage, when said delivery instrument is in said operative disposition, a dispensed portion of said at least one strand being of sufficient length and flexibility to at least partially fill and conform to the interior of the left atrial appendage, said dispensed portion of said at least one strand being of sufficient length and flexibility to define a progressively formed arbitrarily intermingled array of said occlusion material within the interior of the left atrial appendage, said cover structure structurally adapted for disposition in a covering orientation, wherein said covering orientation comprises said cover structure disconnected from said delivery instrument and disposed in covering relation to an entrance to the left atrial appendage, said cover structure comprising a plurality of ribs movable between a collapsed orientation and an expanded orientation, at least a majority of said plurality of ribs including a gripping member movably connected to a free distal end thereof, said collapsed orientation comprising said gripping members disposed in substantially coplanar relation with a remainder of corresponding ones of said distal ends when within an interior of said delivery instrument, said expanded orientation further comprises each of said gripping members biased transversely outward from corresponding ones of said distal ends, when said cover structure is in said expanded orientation, wherein said at least one strand forming the arbitrarily intermingled array is not attached to itself along its length and is not attached to tissue portions of the heart corresponding to the left atrial appendage when the cover structure is in said covering orientation, and wherein when in the covering orientation, each of said plurality of ribs extend radially outwardly and do not project distally of a distal end of a distal end portion.

19. An assembly structured to perform an occlusion of the left atrial appendage, said assembly comprising:

a delivery instrument structured for operative disposition in communicating relation with an interior of the left atrial appendage, said delivery instrument including a cover structure removably connected thereto, occlusion material comprising at least one elongated strand of flexible material mounted on said delivery instrument, said delivery instrument operative for progressive axial dispensing of the length of said at least one strand therefrom into the interior of the left atrial appendage, when said delivery instrument is in said operative disposition, a dispensed portion of said at least one strand being of sufficient length and flexibility to define a progressively formed arbitrarily intermingled array of said occlusion material within the interior of the left atrial appendage, said cover structure being structurally adapted to be disposed in a covering orientation, wherein said covering orientation comprises said cover structure disconnected from said delivery instrument and disposed in covering relation to an entrance to the left atrial appendage, said covering orientation comprising at least a portion of said cover structure disposed exteriorly of the entrance of the left atrial appendage, said at least one strand including a proximal end and a distal end each remaining connected to said cover structure concurrent to said cover structure being in said covering orientation, said cover structure comprising a plurality of ribs movable between a collapsed orientation and an expanded orientation, at least a majority of said plurality of ribs including a gripping member movably connected to a free distal end thereof, said collapsed orientation comprising said gripping members disposed in substantially coplanar relation with a remainder of corresponding ones of said distal ends on an interior of said delivery instrument, and said expanded orientation further comprising each of said gripping members biased transversely outward from corresponding ones of said distal ends, when said cover structure is in said expanded orientation, wherein said at least one strand forming the arbitrarily intermingled array is not attached to itself along its length and is not attached to tissue portions of the heart corresponding to the left atrial appendage when the cover structure is in said covering orientation, and wherein when in the covering orientation, each of said plurality of ribs extend radially outwardly and do not project distally of a distal end of a distal end portion.

* * * * *